(12) United States Patent
Sharma et al.

(10) Patent No.: US 9,815,907 B2
(45) Date of Patent: *Nov. 14, 2017

(54) BINDING PARTNERS SPECIFIC FOR VITAMIN D EPIMERS

(71) Applicant: Siemens Healthcare Diagnostics Inc., Tarrytown, NY (US)

(72) Inventors: Manoj Sharma, Hockessin, DE (US); Tatiana Mareeva, Haddonfield, NJ (US); Yuriy Smirnov, Haddonfield, NJ (US); William D. Bedzyk, Odessa, DE (US); Zhu Teng, Garnet Valley, PA (US); Tie Quan Wei, Wilmington, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/319,221

(22) PCT Filed: Jun. 22, 2015

(86) PCT No.: PCT/US2015/036907
§ 371 (c)(1),
(2) Date: Dec. 15, 2016

(87) PCT Pub. No.: WO2015/200182
PCT Pub. Date: Dec. 30, 2015

(65) Prior Publication Data
US 2017/0121426 A1    May 4, 2017

Related U.S. Application Data

(60) Provisional application No. 62/018,012, filed on Jun. 27, 2014.

(51) Int. Cl.
*G01N 33/82* (2006.01)
*G01N 33/532* (2006.01)
(Continued)

(52) U.S. Cl.
CPC .......... *C07K 16/44* (2013.01); *B01D 15/3809* (2013.01); *G01N 33/82* (2013.01); *C07K 2317/33* (2013.01)

(58) Field of Classification Search
CPC ...... G01N 33/82; G01N 21/76; G01N 33/532; C07C 401/00; C07F 5/003; A61K 39/385;
(Continued)

(56) References Cited

U.S. PATENT DOCUMENTS 6,455,714 B1    9/2002 Holick et al.
6,787,660 B1    9/2004 Armbruster et al.
(Continued)

FOREIGN PATENT DOCUMENTS

EP    0794175 A2    9/1997
WO    2005067673 A2    7/2005
(Continued)

OTHER PUBLICATIONS

International Search Report and Written Opinion of International Application No. PCT/US2015/036907 dated Sep. 16, 2015.
(Continued)

*Primary Examiner* — Shafiqul Haq
(74) *Attorney, Agent, or Firm* — Cynthia G. Tymeson

(57) ABSTRACT

Antibodies are raised against compounds of Formula (I) where Z is an immunogenic carrier. These compounds are capable of binding specifically to corresponding antibodies. The antibodies are specific for epimers of vitamin D. Antibodies in accordance with the principles described herein may be employed to minimize or eliminate 3-epimer cross-
(Continued)

reactivity in assays for non-epimeric forms of vitamin D analytes. Over-estimation of total non-epimeric vitamin D analyte caused by the cross-reactivity of 3-epimer vitamin D with an antibody for vitamin D analyte can be substantially avoided employing, as blocking agents, antibodies prepared against immunogens that are a compound of the Formula (I) wherein Z is an immunogenic carrier.

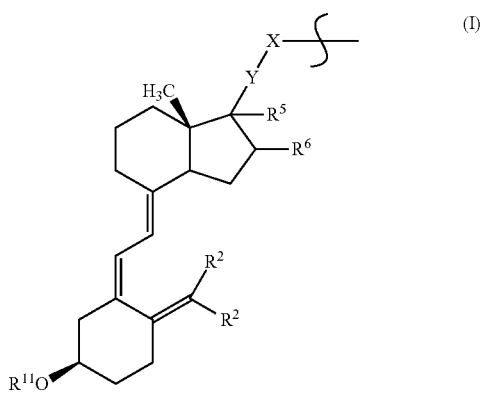

6 Claims, 10 Drawing Sheets

(51) Int. Cl.
  *C07K 16/44* (2006.01)
  *B01D 15/38* (2006.01)
(58) Field of Classification Search
  CPC ........ Y10T 436/203332; A01B 12/006; C07K 16/00
  See application file for complete search history.

(56) References Cited

U.S. PATENT DOCUMENTS

| 8,133,694 B2* | 3/2012 | Armbruster ............ G01N 33/82 435/7.1 |
| 9,244,083 B2* | 1/2016 | Teng ...................... G01N 33/82 |
| 2010/0144671 A1 | 6/2010 | Swamy |
| 2013/0059825 A1 | 3/2013 | Sahakian et al. |
| 2014/0242615 A1 | 8/2014 | Wei et al. |
| 2014/0308751 A1 | 10/2014 | Wei et al. |

FOREIGN PATENT DOCUMENTS

| WO | 2013172967 A1 | 11/2013 |
| WO | 2014085486 A2 | 6/2014 |
| WO | 2015200178 A1 | 12/2015 |

OTHER PUBLICATIONS

Jinge Zhu et al., "Screening of Selective Inhibitors of 1α,25-Dihydroxyvitamin D3 24-Hydroxylase Using Recombinant Human Enzyme Expressed in *Escherichia coli*", Nov. 8, 2010, Biochemistry, 49 (49), pp. 10403-10411.
Molnar et al., "1α,25(OH)2-3-Epi-Vitamin D3, a Natural Physiological Metabolite of Vitamin D3: Its Synthesis, Biological Activity and Crystal Structure with Its Receptor", Mar. 2011, PLOS One, Volumn 6, Issue 3, e18124, pp. 1-11.
Moon et al., "Comparison of four current 25-hydroxyvitamin D assays", 2012, Clinical Biochemistry 45, pp. 326-330.
Ouweland et al., "C3-epimer cross-reactivity of automated 25-hydroxyvitamin D immunoassays", 2013, Ned Tijdschr Klin Chem Labgeneesk, vol. 3, No. 3, pp. 136-138.
Farrell et al., "Determination of vitamin D and its metabolites", 2013, Best Practice & Research Clinical Endocrinology & Metabolism 27, pp. 678-688.
European Search Report and Search Opinion of European Application No. 15811774.7 dated May 23, 2017.
European Search Report and Search Opinion of European Application No. 15812575.7 dated May 11, 2017.
European Search Report and Search Opinion of European Application No. 15812129.3 dated Jul. 25, 2017.
Strathmann et al., "Quantification of 1α,25 Dihydroxy Vitamin D by Immunoextraction and Liquid Chromatography-Tandem Mass Spectrometry", Sep. 2011, Clin Chem.; 57(9): pp. 1279-1285.
Bailey et al., "Analytical Measurement and Clinical Relevance of Vitamin D(3) C3-Epimer", Feb. 2013, Clinical Biochemistry;46(3): pp. 190-196.
van den Ouweland et al., "Evaluation of 3-epi-25-hydroxyvitamin D3 Cross-Reactivity in the Roche Elecsys Vitamin D Total Protein Binding Assay", Mar. 2014, Clin Chem Lab Med; 52(3): pp. 373-380.
Freeman et al., "Performance Evaluation of Four 25-hydroxyvitamin D Assays to Measure 25-hydroxyvitamin D2", Nov. 2015, Clin Biochem.; 48(16-17): pp. 1097-1104.
Laha et al., "Characterizing Antibody Cross-Reactivity for Immunoaffinity Purification of Analytes prior to Multiplexed Liquid Chromatography-Tandem Mass Spectrometry", 2012, Clinical Chemistry 58(12): pp. 1711-1716.
Akira Kambegawa, "Enzyme Labeling Methods and it's Specificities", 1995, Nippon Rinsho 53(9): pp. 66-71. See English Abstract.

* cited by examiner 25-hydroxyvitamin D$_3$ 3-epi-25-hydroxyvitamin D$_3$ 25-hydroxyvitamin D$_2$ 3-epi-25-hydroxyvitamin D$_2$

BINDING PARTNERS SPECIFIC FOR VITAMIN D EPIMERS

The subject application claims benefit under 35 USC §119(e) of U.S. provisional Application No. 62/018,012, filed Jun. 27, 2014. The entire contents of the above-referenced patent application are hereby expressly incorporated herein by reference.

BACKGROUND

This invention relates to compositions, methods and kits for determining the presence and/or amount of vitamin D analytes, including vitamin D isomers, and metabolites thereof, in a sample suspected of containing the same. More particularly, the invention relates to binding partners such as, for example, antibodies, specific for epimers of vitamin D.

Many small molecule compounds or haptens such as, for example, drugs and vitamins, exist in isomeric forms, of which only one form is active. In order to obtain an accurate measurement of the active form of an analyte, the presence of the non-active isomer of the analyte must be addressed. Measurements of both isomeric forms of an analyte, that is, active and non-active forms, can lead to inaccuracies that may be detrimental to an individual depending on the function of the active form of the analyte. Accurately assessing the level of each of a pair of isomeric analytes in biological samples is important especially where only one of the isomers is active and measurements that include the amount of the non-active isomer distort the level of the analyte in a sample. For example, measuring vitamin D levels in biological samples is important since vitamin D deficiency is related to a number of disorders in mammals. In infants, for example, vitamin D measurements that include amounts of 3-epi isomers can lead to inaccurate assessment of vitamin D levels in the infant, which in turn can lead to a lack of proper supplementation. It is important to measure the active form of vitamin D so that an infant can receive proper vitamin D therapy, if necessary.

The term "vitamin D" refers to a group of fat-soluble secosteroids. In humans, vitamin D is unique because it can be ingested as cholecalciferol (vitamin $D_3$) or ergocalciferol (vitamin $D_2$) and because the body can also synthesize it (from cholesterol) when sun exposure is adequate. Because of this latter property, vitamin D is considered by some to be a non-essential dietary vitamin although most consider it an essential nutrient. Vitamin D has an important physiological role in the positive regulation of calcium ion homeostasis. Vitamin $D_3$ is the form of the vitamin synthesized by animals. It is also a common supplement added to milk products and certain food products as is vitamin $D_2$.

Both dietary and intrinsically synthesized vitamin $D_3$ must undergo metabolic activation to generate bioactive metabolites. In humans, the initial step of vitamin $D_3$ activation occurs primarily in the liver and involves hydroxylation to form the intermediate metabolite 25-hydroxycholecalciferol. Calcidiol is the major form of Vitamin $D_3$ in the circulatory system. Vitamin $D_2$ also undergoes similar metabolic activation to 25-hydroxyvitamin $D_2$. Collectively these compounds are called 25-hydroxyvitamin D (abbreviated 25(OH)D) and they are the major metabolites that are measured in serum to determine vitamin D status; 25(OH)D and its epimers are both pre-hormones that need to be converted into 1,25(OH)D to exert biological functions. The comparison of bioactivity of 1,25(OH)D versus that of 3-epi-1,25(OH)D is complex.

The vitamin D compounds 25-hydroxyvitamin $D_3$ and 25-hydroxyvitamin $D_2$ are epimeric at the 3-position with the epimers being designated 25-hydroxyvitamin $D_3$ and 3-epi-25-hydroxyvitamin $D_3$ and 25-hydroxyvitamin $D_2$ and 3-epi-25-hydroxyvitamin $D_2$, respectively. Only one of the epimers of each of these epimeric compounds, namely, 25-hydroxyvitamin $D_3$ and 25-hydroxyvitamin $D_2$, respectively, are active. The structures for the epimers of 25-hydroxyvitamin $D_3$ and 25-hydroxyvitamin $D_2$ are set forth in FIG. 1.

Assessing vitamin D levels in biological samples is important since vitamin D deficiency is related to a number of disorders in mammals. There is a need for reagents and methods for accurate and sensitive determinations of concentrations of vitamin D and epimeric forms of vitamin D, and metabolites thereof in samples.

SUMMARY

Some examples in accordance with the principles described herein are directed to binding partners such as, for example, antibodies, prepared against a compound of the Formula I:

$(R^1)_p\text{-}(L)_q\text{-}Z$ wherein $R^1 = $ 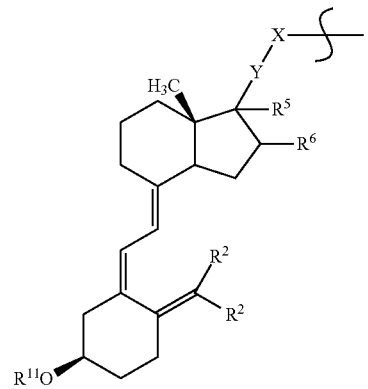

or H, wherein at least one $R^1$ is not H,

Y is O, S, CR, or $NR^4$,

X is —O—$(CH_2)_n$—C(O)—, —$(CH_2)_w$—C(O)—, —$(CH_2)_w$—C(O)—$(CH_2)_x$—C(O)—, —$(CH_2)_w$—C(O)—NH$(CH_2)_y$—C(O)—, —$NR^3$—C(O)—,

R is independently H or alkyl, $R^2$ is independently H or alkyl, $R^3$, $R^4$, $R^5$ and $R^6$ are independently H or alkyl, or $R^4$ and $R^5$ may be taken together to form a bond, or $R^5$ and $R^6$ may be taken together to form a bond, $R^{11}$ is H, alkyl, or acyl, n is an integer from 1 to 10, w is an integer from 0 to 10, x is an integer from 1 to 10, y is an integer from 1 to 10, p is an integer from 1 to 10, L is a linking group, q is 0 or 1, and Z is a poly(amino acid) immunogenic carrier or a non-poly(amino acid) immunogenic carrier.

Some examples in accordance with the principles described herein are directed to antibodies raised against a compound of the Formula II:

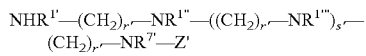

NHR$^{1'}$—(CH$_2$)$_{r'}$—NR$^{1''}$—((CH$_2$)$_{r'}$—NR$^{1'''}$)$_{s'}$—(CH$_2$)$_{r'}$—NR$^{7'}$—Z' wherein
R$^{1'}$, R$^{1''}$ or R$^{1'''}$ are each independently selected from

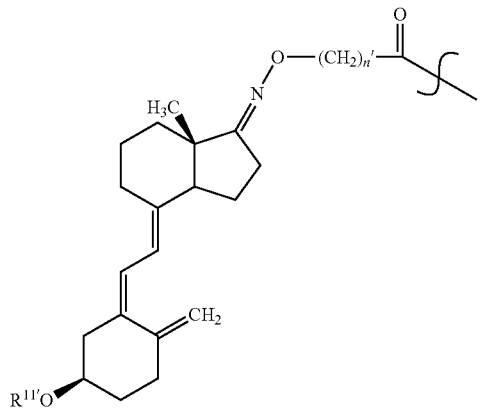

and H,
wherein at least one of R$^{1'}$, R$^{1''}$ or R$^{1'''}$ is not H,
n' is an integer from 1 to 10,
r' is independently an integer from 1 to 10,
s' is an integer from 1 to 10,
R$^{7'}$ is H or alkyl,
R$^{11'}$ is H, alkyl, or acyl, and
Z' is a poly(amino acid) immunogenic carrier or a non-poly(amino acid) immunogenic carrier; or raised against mixtures of two or more of the above compounds.

Some examples in accordance with the principles described herein are directed to antibodies that are specific for 3-epi-25-hydroxyvitamin D$_3$ and do not bind to any detectable degree to non-epi-vitamin D compounds.

BRIEF DESCRIPTION OF DRAWINGS

The drawings provided herein are not to scale and are provided for the purpose of facilitating the understanding of certain examples in accordance with the principles described herein and are provided by way of illustration and not limitation on the scope of the appended claims.

DETAILED DESCRIPTION OF SPECIFIC EMBODIMENTS

Compounds

Figure 1:
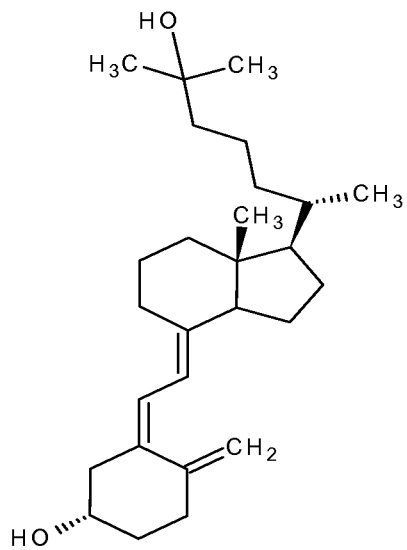
FIG. 1 is a depiction of the chemical formulas for the epimeric forms of 25-hydroxyvitamin D$_3$ and 25-hydroxyvitamin D$_2$.
Figure 1:
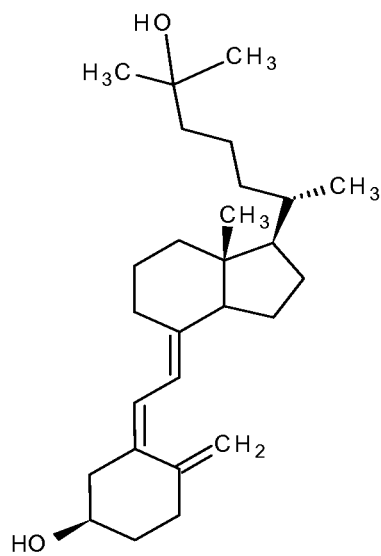
Figure 1:
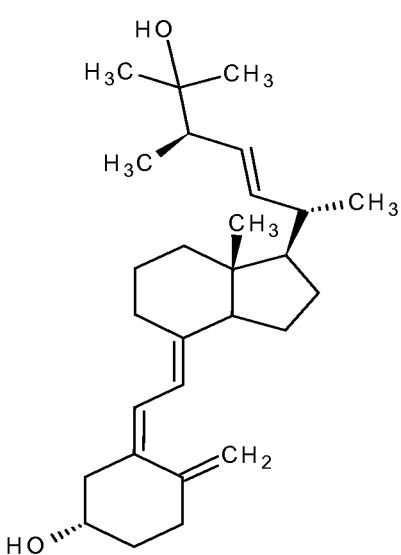
Figure 1:
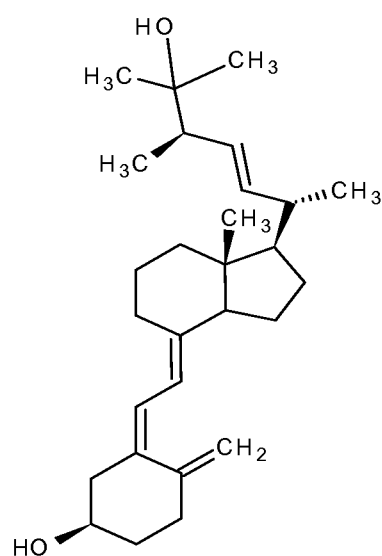

As mentioned above, some examples in accordance with the principles described herein are directed to binding partners, such as, for example, antibodies raised against compounds of the Formula I:

$$(R^1)_p\text{-}(L)_q\text{-}Z$$

wherein

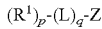

$R^1 =$

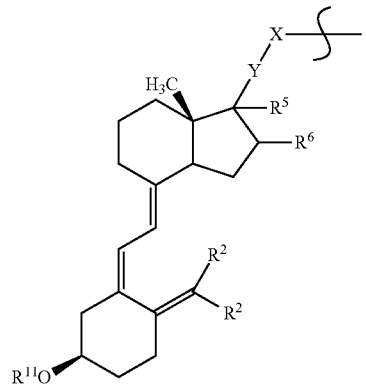

or H, wherein at least one R$^1$ is not H,
Y is O, S, CR, or NR$^4$,
X is —O—(CH$_2$)$_n$—C(O)—, —(CH$_2$)$_w$—C(O)—, or —NR$^3$—C(O)—; in some examples, X is —O—(CH$_2$)$_n$—C(O)— when Y is NR$^4$, for example, —(CH$_2$)$_w$—C(O)—, —(CH$_2$)$_w$—C(O)—(CH$_2$)$_x$—C(O)—, or —(CH$_2$)$_w$—C(O)—NH(CH$_2$)$_y$—C(O)— when Y is O or S, for example, or —NR$^3$—C(O)— when Y is CR, for example,
R is independently H or alkyl,
R$^2$ is independently H or alkyl,
R$^3$, R$^4$, R$^5$ and R$^6$ are independently H or alkyl, or R$^4$ and R$^5$ may be taken together to form a bond, or R$^5$ and R$^6$ may be taken together to form a bond,
R$^{11}$ is H, alkyl, or acyl,
n is an integer from 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example,
w is an integer from 0 to 10, 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example, x is an integer from 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example, y is an integer from 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example, p is an integer from 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example, L is a linking group, q is 0 or 1, and Z is a poly(amino acid) immunogenic carrier moiety or a non-poly(amino acid) immunogenic carrier moiety.

As used herein, the term "alkyl" includes those alkyl groups of a designated number of carbon atoms of either a straight, branched, or cyclic configuration. Examples of "alkyl" include, but are not limited to, methyl, ethyl, propyl, isopropyl, butyl, sec- and tert-butyl, pentyl, hexyl, heptyl, cyclopropyl, cyclobutyl, cyclopentyl, cyclohexyl, cycloheptyl, norbornyl, for example. In some examples, alkyl contains 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, carbon atoms, which may be unsubstituted or one or more of which may be substituted by one or more of hydroxy, alkoxy of 1 to 5, or 1 to 4, of 1 to 3, or 1 to 2, or 2 to 5, or 2 to 4, or 2 to 3, or 3 to 5, or 3 to 4, or 4 to 5 carbon atoms.

As used herein, the term "acyl" means $R^{12}C(O)$— where $R^{12}$ is alkyl or aryl.

As used herein, the term "aryl" means an organic radical derived from an aromatic hydrocarbon by the removal of one atom and containing one or more aromatic rings, usually one to four aromatic rings, such as, e.g., phenyl (from benzene), naphthyl (from naphthalene), etc., e.g., phenyl, naphthyl, phenanthryl.

As used herein, the phrase "linking group" refers to a chemical moiety that may comprise about 2 to about 50 atoms, or 4 to about 30 atoms, not counting hydrogen and may comprise a chain of from 2 to about 30 atoms, or 3 to about 20 atoms, each independently selected from the group normally consisting of carbon, oxygen, sulfur, nitrogen, and phosphorous. In some examples, part or all of the linking group may be a portion of the molecule being linked such as, but not limited to, an amino acid residue on a poly(amino acid), for example. The number of heteroatoms in the linking group may be in the range from 0 to about 20, or 1 to about 15, or about 2 to about 10. The linking group may be aliphatic or aromatic. When heteroatoms are present, oxygen is normally present as oxo or oxy, bonded to carbon, sulfur, nitrogen or phosphorous, nitrogen is normally present as nitro, nitroso or amino, normally bonded to carbon, oxygen, sulfur or phosphorous; sulfur is analogous to oxygen; while phosphorous is bonded to carbon, sulfur, oxygen or nitrogen, usually as phosphonate and phosphate mono- or diester. Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters.

For the most part, when a linking group has a linking functionality (functionality for reaction with a moiety) such as, for example, a non-oxocarbonyl group including nitrogen and sulfur analogs, a phosphate group, an amino group, alkylating agent such as halo or tosylalkyl, oxy (hydroxyl or the sulfur analog, mercapto) oxocarbonyl (e.g., aldehyde or ketone), or active olefin such as a vinyl sulfone or α-, β-unsaturated ester, these functionalities are linked to amine groups, carboxyl groups, active olefins, alkylating agents, e.g., bromoacetyl. Where an amine and carboxylic acid or its nitrogen derivative or phosphoric acid are linked, amides, amidines and phosphoramides are formed. Where mercaptan and activated olefin are linked, thioethers are formed. Where a mercaptan and an alkylating agent are linked, thioethers are formed. Where aldehyde and an amine are linked under reducing conditions, an alkylamine is formed. Where a ketone or aldehyde and a hydroxylamine (including derivatives thereof where a substituent is in place of the hydrogen of the hydroxyl group) are linked, an oxime functionality (=N—O—) is formed. Where a carboxylic acid or phosphate acid and an alcohol are linked, esters are formed.

As used herein, the term "immunogenic carrier" means a group or moiety that is conjugated to a hapten. The conjugate of the immunogenic carrier and the hapten may be injected into an organism capable of eliciting an immune response such as, but not limited to, a mammal, an avian (e.g., chicken or pigeon), an amphibian, or a reptile; or the conjugate may be used to inoculate an in vitro sample (mammalian, including human, avian, amphibian or reptile) or otherwise may be employed in a technique to produce a binding partner for the hapten. The phrase "binding partner" refers to a molecule that is a member of a specific binding pair, which is one of two different molecules that specifically binds to and is thereby defined as complementary with the other molecule. For example, one member of the specific binding pair may have an area on the surface or in a cavity that specifically binds to a particular spatial and polar organization of the other member of the specific binding pair. The binding partner may be, by way of illustration and not limitation, an antibody or an aptamer (e.g., nucleic acid aptamer or peptide aptamer), for example. In one example, an immunogenic carrier may be employed as an immunogen to induce an immune response and elicit production of a binding partner for a hapten. Other techniques include phage display and in vitro selection. Immunogenic carriers are also sometimes referred to as antigenic carriers. In some examples in accordance with the principles described herein, immunogens comprising immunogenic carriers, including poly(amino acid) and non-poly(amino acid) immunogenic carriers, are synthesized and used to prepare antibodies. Haptens are compounds capable of binding specifically to corresponding antibodies, but do not themselves act as immunogens (or antigens) for preparation of the antibodies. Consequently, a hapten is linked to an immunogenic carrier, which may be employed, for example, to raise antibodies.

The molecular weight range (in Daltons) for poly(amino acids) that are immunogenic carriers is about 5,000 to about 10,000,000, or about 20,000 to about 600,000, or about 25,000 to about 250,000, for example. "Poly(amino acid) immunogenic carrier moieties" include proteins such as, for example, albumins, serum proteins, e.g., globulins, ocular lens proteins and lipoproteins. Illustrative proteins include, but are not limited to, bovine serum albumin (BSA), keyhole limpet hemocyanin (KLH), egg ovalbumin, and bovine gamma-globulin (BGG), for example. "Non-poly(amino acid) immunogenic carrier moieties" include polysaccharides, nucleic acids and particles (biologic and synthetic materials). A wide variety of immunogenic carriers are disclosed in Davalian, et al., U.S. Pat. No. 5,089,390, column 4, line 57 to column 5, line 5, which is incorporated herein by reference.

As mentioned above, the immunogenic carrier moiety may be a polysaccharide, which is a high molecular weight polymer of monosaccharides that may be prepared naturally or synthetically and usually involves repeated condensations of monosaccharides. Examples of polysaccharides are starches, glycogen, cellulose, carbohydrate gums, such as gum arabic, agar, and so forth. The polysaccharide can also contain poly(amino acid) residues and/or lipid residues.

As used herein, the term "label" includes poly(amino acid) labels and non-poly(amino acid) labels. The term "poly(amino acid) label moieties" includes labels that are proteins such as, but not limited to, enzymes, antibodies, peptides, and immunogens, for example. With label proteins such as, for example, enzymes, the weight average molecular weight range will be from about 10,000 to about 600,000 or from about 10,000 to about 300,000. There is usually at least one compound in accordance with the principles described herein (analog group) per about 200,000 molecular weight, or at least about 1 per about 150,000 molecular weight, or at least about 1 per about 100,000 molecular weight, or at least about 1 per about 50,000 molecular weight, or at least about 1 per 40,000, molecular weight, or at least about 1 per 30,000 molecular weight, or at least 1 per 20,000 molecular weight, or at least one per 10,000 molecular, or at least one per 5,000 molecular weight, for example, of the protein. In the case of enzymes, the number of analog groups is usually from 1 to about 20, about 2 to about 15, about 3 to about 12, or about 6 to about 10.

Enzymes include, by way of illustration and not limitation, redox enzymes such as, for example, dehydrogenases, e.g., glucose-6-phosphate dehydrogenase (G6PDH) and lactate dehydrogenase; enzymes that involve the production of hydrogen peroxide and the use of the hydrogen peroxide to oxidize a dye precursor to a dye such as, for example, horseradish peroxidase, lactoperoxidase and microperoxidase; hydrolases such as, for example, alkaline phosphatase and β-galactosidase; luciferases such as, for example firefly luciferase, and bacterial luciferase; transferases; combinations of enzymes such as, but not limited to, saccharide oxidases, e.g., glucose and galactose oxidase, or heterocyclic oxidases, such as uricase and xanthine oxidase, coupled with an enzyme that employs hydrogen peroxide to oxidize a dye precursor, that is, a peroxidase such as horseradish peroxidase, lactoperoxidase or microperoxidase, for example.

As used herein, the term "non-poly(amino acid) labels" includes those labels that are not proteins. The non-poly (amino acid) label is capable of being detected directly or is detectable through a reaction that produces a detectable signal. The non-poly(amino acid) label can be isotopic or non-isotopic and can be, by way of illustration and not limitation, a radioisotope, a luminescent compound (which includes, but is not limited to fluorescent compounds and chemiluminescent compounds, for example), a polynucleotide coding for a catalyst, a promoter, a dye, a coenzyme, an enzyme substrate, a radioactive group, a small organic molecule (molecular weight 200 to 2,000), a particle, and an amplifiable polynucleotide sequence, for example.

As mentioned above, a "small organic molecule" has a molecular weight of about 200 to about 2,000, or about 200 to about 1,500, or about 200 to about 1,000, or about 200 to about 500. Such "small organic molecules" include, but are not limited to, biotin, fluorescent molecules (such as fluorescein and rhodamine, for example), chemiluminescent molecules, and dinitrophenol, for example. A binding partner for a small organic molecule is a molecule that specifically recognizes and binds to the small molecule. Binding partners for a small molecule are defined by the nature of the small molecule and include, but are not limited to, avidin, streptavidin, antibody for the small organic molecule (which include, but are not limited to, antibody for a fluorescent molecule (such as antibody for fluorescein and antibody for rhodamine, for example), antibody for a chemiluminescent molecule, and antibody for dinitrophenol, for example.

As used herein, the terms "non-label poly(amino acid) moiety" and "non-immunogenic carrier poly(amino acid) moiety" refer to poly(amino acids) that are not normally considered labels or immunogenic carriers although such moieties may be labels or immunogenic carriers in certain circumstances. For example, an antibody may not be considered a label but may be a label if the antibody is modified to include a signal producing moiety or part of a signal producing system. Furthermore, an antibody may not be considered as an immunogenic carrier but is nonetheless capable of being an immunogenic carrier in certain circumstances because of it higher molecular weight.

In some examples the non-poly(amino acid) label may be selected from the group consisting of supports, magnetic particles, acridinium esters, a combination of magnetic particles and acridinium esters (such as, for example, acridinium ester labeled paramagnetic particles), chemiluminescent particles and sensitizer particles.

The term "covalent" refers to attachment of molecules such as by a direct connection, e.g., a chemical bond between the molecules. The term "non-covalent" refers to attachment of molecules involving specific binding between complementary specific binding pair (sbp) members that are attached to the molecules.

In some examples compounds in accordance with the principles described herein may be associated with a support, for example, by covalent or non-covalent binding. As mentioned above, in some examples in accordance with the principles described herein, $R^2$ may be a support, which may be comprised of an organic or inorganic, solid or fluid, water insoluble material and which may be transparent or partially transparent. The support can have any of a number of shapes, such as, but not limited to, a particle (particulate support) including bead, a film, a membrane, a tube, a well, a strip, a rod, a fiber, or a planar surface such as, e.g., a plate or paper, for example. The support may or may not be suspendable in the medium in which it is employed. Examples of suspendable supports are polymeric materials such as latex, lipid bilayers or liposomes, oil droplets, cells and hydrogels, and magnetic particles, for example. Other support compositions include polymers, such as, by way of illustration and not limitation, nitrocellulose, cellulose acetate, poly (vinyl chloride), polyacrylamide, polyacrylate, polyethylene, polypropylene, poly(4 methylbutene), polystyrene, polymethacrylate, poly(ethylene terephthalate), nylon, poly(vinyl butyrate), for example, either used by themselves or in conjunction with other materials. The support may or may not be further labeled with a dye, catalyst or other detectable group, for example.

In some examples in accordance with the principles described herein, the support may be a particle. The particles have an average diameter of at least about 0.02 microns and not more than about 100 microns. In some examples, the particles have an average diameter from about 0.05 microns to about 20 microns, or from about 0.3 microns to about 10 microns. The particle may be organic or inorganic, swellable or non-swellable, porous or non-porous, preferably of a density approximating water, generally from about 0.7 g/mL to about 1.5 g/mL, and composed of material that can be transparent, partially transparent, or opaque. The particles can be biological materials such as cells and microorganisms, e.g., erythrocytes, leukocytes, lymphocytes, hybridomas, *streptococcus, Staphylococcus aureus*, and *E. coli*, viruses, for example. The particles can also be particles comprised of organic and inorganic polymers, liposomes, latex particles, magnetic or non-magnetic particles, phospholipid vesicles, chylomicrons, lipoproteins, and the like. In some examples, the particles are chromium dioxide (chrome) particles or latex particles.

Magnetic particles include paramagnetic particles, ferromagnetic particles and diamagnetic particles. Such particles include, but are not limited to, transition metals of periods 4-7 of the Periodic Table including chromium, copper, cobalt, aluminum, manganese, iron, and nickel, for example.

Chemiluminescent particles are particles that have associated therewith a chemiluminescent compound. The phrase "associated therewith" as used herein means that a compound such as, for example, a chemiluminescent compound and a particle may be associated by direct or indirect bonding, adsorption, absorption, incorporation, or solution, for example. Examples of chemiluminescent compounds that may be utilized are those set forth in U.S. Pat. Nos. 5,340,716 and 6,251,581, the relevant disclosures of which are incorporated herein by reference. In some examples in accordance with the principles described herein, the chemiluminescent compound is a photoactivatable substance that undergoes a chemical reaction upon direct or sensitized excitation by light or upon reaction with singlet oxygen to form a metastable reaction product that is capable of decomposition with the simultaneous or subsequent emission of light, usually within the wavelength range of 250 to 1200 nm. The term "photoactivatable" includes "photochemically activatable". In some examples, the chemiluminescent compounds are those that react with singlet oxygen to form dioxetanes or dioxetanones. The latter are usually electron rich olefins. Exemplary of such electron rich olefins are enol ethers, enamines, 9-alkylidene-N-alkylacridans, arylvinylethers, dioxenes, arylimidazoles, 9-alkylidene-xanthanes and lucigenin. Other compounds include luminol and other phthalhydrazides and chemiluminescent compounds that are protected from undergoing a chemiluminescent reaction by virtue of their being protected by a photochemically labile protecting group, such compounds including, for example, firefly luciferin, aquaphorin, and luminol. Examples of such chemiluminescent compounds that may be utilized are those set forth in U.S. Pat. No. 5,709,994, the relevant disclosure of which is incorporated herein by reference.

Sensitizer particles are particles that have associated therewith a sensitizer compound, which includes, but is not limited to, a photosensitizer compound. Examples of sensitizer compounds that may be utilized are those set forth in U.S. Pat. Nos. 5,340,716 and 6,251,581, the relevant disclosures of which are incorporated herein by reference.

A photosensitizer is a sensitizer for generation of singlet oxygen usually by excitation with light. In some examples, the photosensitizer absorbs at a longer wavelength than the chemiluminescent compound and has a lower energy triplet than the chemiluminescent compound. The photosensitizer can be photoactivatable (e.g., dyes and aromatic compounds). The photosensitizer is usually a compound comprised of covalently bonded atoms, usually with multiple conjugated double or triple bonds. The compound should absorb light in the wavelength range of 200-1100 nm, usually 300-1000 nm, preferably 450-950 nm. Typical photosensitizers include, but are not limited to, acetone, benzophenone, 9-thioxanthone, eosin, 9,10-dibromoanthracene, methylene blue, metallo-porphyrins (e.g., hematoporphyrin), phthalocyanines, chlorophylls, rose bengal, buckminsterfullerene, for example, and derivatives of these compounds. Examples of other photosensitizers are enumerated in N.J. Turro, "Molecular Photochemistry", page 132, W. A. Benjamin Inc., N.Y. 1965. The photosensitizer assists photoactivation where activation is by singlet oxygen. Usually, the photosensitizer absorbs light and the thus formed excited photosensitizer activates oxygen to produce singlet oxygen, which reacts with the chemiluminescent compound to give a metastable luminescent intermediate.

In the formulas set forth herein, a squiggle line through a bond indicates the point of attachment of a moiety in the formula.

Some examples in accordance with the principles described herein are directed to binding partners such as, for example, antibodies raised against Formula IV compounds, which are compounds of Formula I wherein:

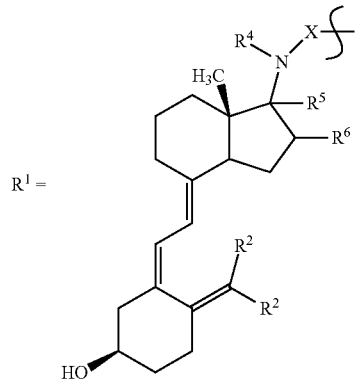

or H, wherein at least one $R^1$ is not H; or raised against mixtures of two or more of the above compounds.

Some examples in accordance with the principles described herein are directed to binding partners such as, for example, antibodies raised against derivatives of (7aS,E)-4-((Z)-2-((R)-5-hydroxy-2-methylene-cyclohexylidene)ethylidene)-7a-methyloctahydro-1H-inden-1-one (HM- CHEMOIO derivatives), or Formula V compounds, which are compounds of Formula I wherein:

$R^1 =$

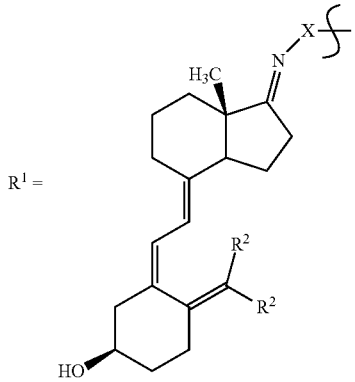

or H, wherein at least one $R^1$ is not H; or raised against mixtures of two or more of the above compounds.

Some examples in accordance with the principles described herein are directed to antibodies raised against Formula VI compounds, which are compounds of Formula I wherein:

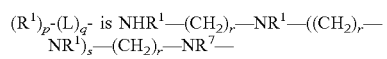

wherein $R^1$ is independently

VIa

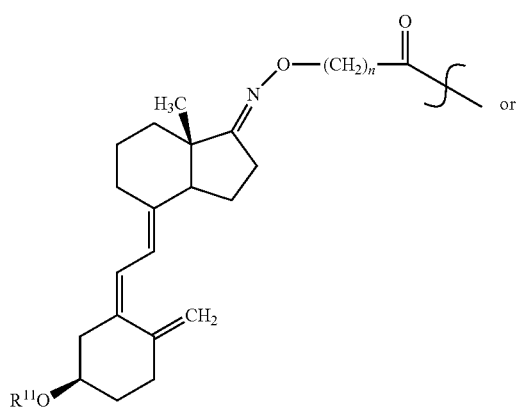

or

VIb

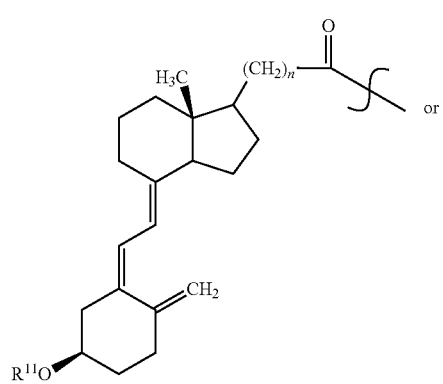

or

VIc

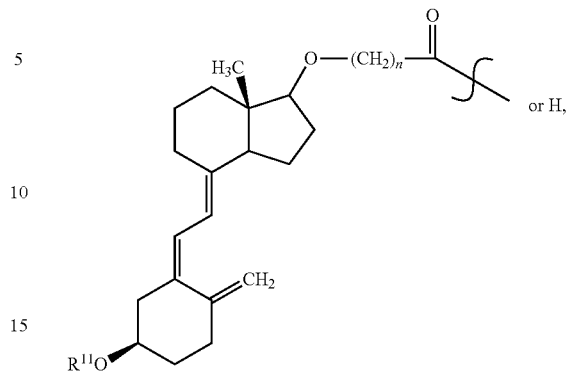

or H, wherein at least one $R^1$ is not H, p, q and n are as defined above, r is independently an integer from 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example, s is an integer from 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example, and $R^7$ is H or alkyl; or raised against mixtures of two or more of the above compounds.

Some examples in accordance with the principles described herein are directed to binding partners such as, for example, antibodies raised against compounds of Formula II:

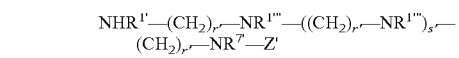

wherein $R^{1'}$, $R^{1''}$ or $R^{1'''}$ are each independently selected from the group consisting of

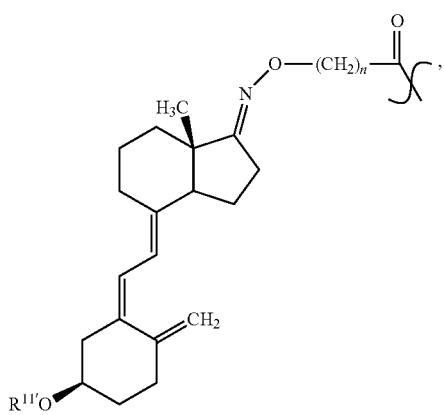

IIa

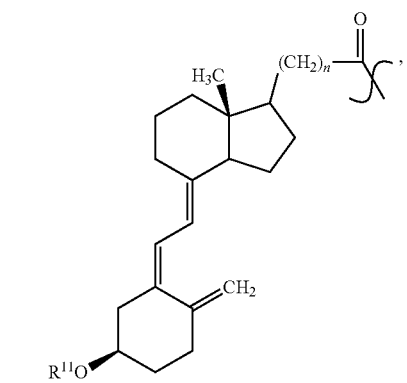

IIb

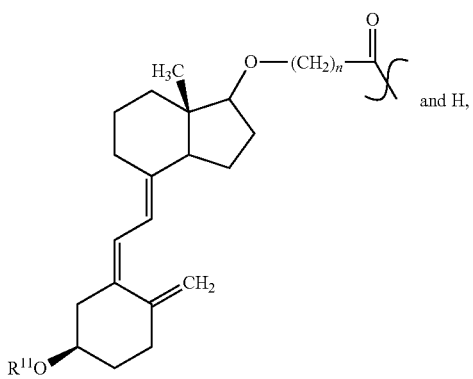

IIc and H, wherein at least one of R$^{1'}$, R$^{1''}$ or R$^{1'''}$ is not H, n and w are as defined above, r' is independently an integer from 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example, s' is an integer from 1 to 10, or 1 to 9, or 1 to 8, or 1 to 7, or 1 to 6, or 1 to 5, or 1 to 4, or 1 to 3, or 1 to 2, or 2 to 10, or 2 to 9, or 2 to 8, or 2 to 7, or 2 to 6, or 2 to 5, or 2 to 4, or 2 to 3, or 3 to 10, or 3 to 9, or 3 to 8, or 3 to 7, or 3 to 6, or 3 to 5, or 3 to 4, or 4 to 10, or 4 to 9, or 4 to 8, or 4 to 7, or 4 to 6, or 4 to 5, or 5 to 10, or 5 to 9, or 5 to 8, or 5 to 7, or 5 to 6, or 6 to 10, or 6 to 9, or 6 to 8, or 6 to 7, or 7 to 10, or 7 to 9, or 7 to 8, or 8 to 10, or 8 to 9, or 9 to 10, for example, R$^{7'}$ is H or alkyl, R$^{11'}$ is H, alkyl, or acyl, and Z' is a poly(amino acid) immunogenic carrier or a non-poly(amino acid) immunogenic carrier; or raised against mixtures of two or more of the above compounds.

In some examples s' is 1. In some examples R$^{7'}$ is H. In some examples r' is 2. In some examples R$^{1''}$ and R$^{1'''}$ are H; in some examples R$^{1'}$ and R$^{1'''}$ are H; and in some examples R$^{1'}$ and R$^{1''}$ are H. In some examples none of R$^{1'}$, R$^{1''}$ and R$^{1'''}$ is H, that is, R$^{1'}$, R$^{1''}$ and R$^{1'''}$ are all

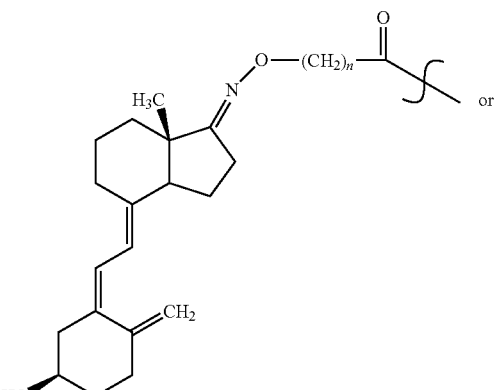

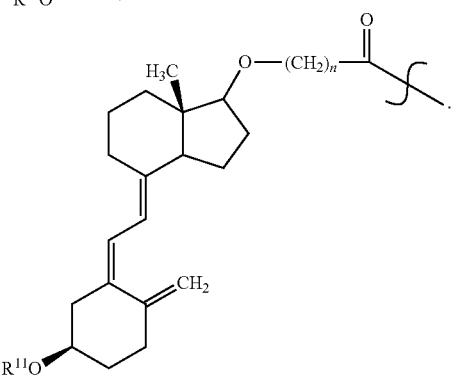

Some examples in accordance with the principles described herein are directed to pharmaceutical compositions comprising an effective amount of an antibody in accordance with the principles described herein.

Preparation of Compounds

Examples of methods of preparing compounds that are HMCHEMOIO derivatives in accordance with the principles described herein are discussed below, by way of illustration and not limitation. Other approaches may be employed to form the above compounds and other compounds consistent with the principles described herein.

Figure 2:
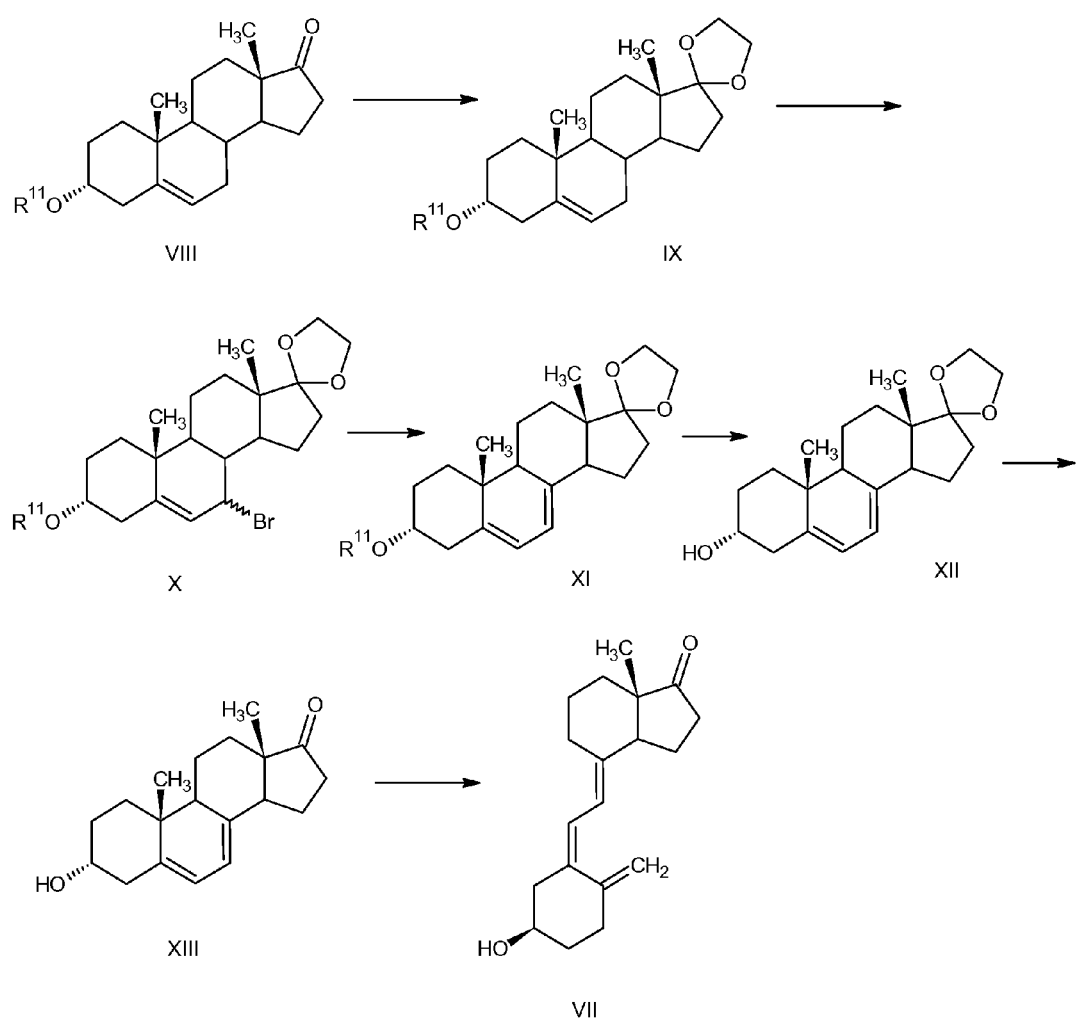
FIG. 2 is a schematic diagram of a synthesis of compounds in accordance with examples in accordance with the principles described herein.

An example of a preparation of a compound of Formula VII ((7aS,E)-4-((Z)-2-((R)-5-hydroxy-2-methylenecyclohexylidene)ethylidene)-7a-methyloctahydro-1H-inden-1-one) is set forth in FIG. 2. Referring to FIG. 2, compound of the Formula VIII, wherein $R^{11}O$ is acetyl, is treated to form ketal of Formula IX. In one example, compound of the Formula VIII is treated with ethylene glycol in an aromatic solvent such as benzene in the presence of a strong organic acid such as, for example, p-toluene sulfonic acid, under conditions (temperature and time) for forming a ketal. In some examples the reaction is conducted at reflux for a period of about 10 hours to about 24 hours, or about 12 to about 20 hours.

Compound of the Formula IX is treated to introduce a halide group such as, for example, a chloride group or a bromide group. In one example, compound of Formula IX is treated with N-bromosuccinimide and a free radical initiator such as, for example, azobisisobutyronitrile in an organic solvent such as, for example, an alkane (e.g., hexane), for example, under conditions for introducing a bromide group into the compound of Formula IX to give a compound of the Formula X. In some examples the reaction is conducted at reflux for about 30 minutes.

The halide of the compound of Formula X is removed to give a compound of the Formula XI having two double bonds that are conjugated. In one example, the compound of Formula X is treated with mild base such as, for example, tetra-n-butylammonium fluoride, in a polar organic solvent such as, for example, an ether (e.g., tetrahydrofuran), for example, under conditions for removing a hydrogen halide to form a double bond (compound of Formula XI). In some examples the temperature during the reaction is about 15° C. to about 25° C. The time period of the reaction is about 2 hours.

The acetyl group ($R^{11}$) of the compound of Formula XI is removed by treatment with an inorganic base such as, for example, sodium hydroxide or potassium hydroxide, in a polar organic solvent such as, for example, an alkanol (e.g., methanol or ethanol). The reaction components are subjected to conditions for removing the acetyl group to give compound of the Formula XII. In some examples the temperature during the reaction is about 15° C. to about 25° C., or at room temperature. The time period of the reaction is about 4 hours to about 8 hours.

The ketal group of the compound of Formula XII is removed, for example, using a strong organic acid such as, for example, p-toluene sulfonic acid, in a mixture of water and a polar organic solvent such as, for example, acetone, under conditions for removing a ketal to yield the compound of Formula XIII. In some examples the temperature during the reaction is about 15° C. to about 25° C. The time period of the reaction is about 12 hours to about 48 hours.

The compound of Formula VII is formed by treating the compound of Formula XIII with reagents for opening a ring such as, for example, treatment with UV light (photo reaction) in a polar organic solvent such as, for example, an alkanol (e.g., methanol or ethanol), an ether (e.g., ethyl ether), a ketone (e.g., acetone), or a combination of two or more of the above, under conditions for opening a ring of Formula XIII. In some examples the temperature during the photo reaction is about −20° C. to about 0° C. The time period of the photo reaction is about 1 to about 10 minutes, or about 3 to about 5 minutes. The photo reaction is followed by refluxing the intermediate in ethanol for about 3 hours.

Figure 3:
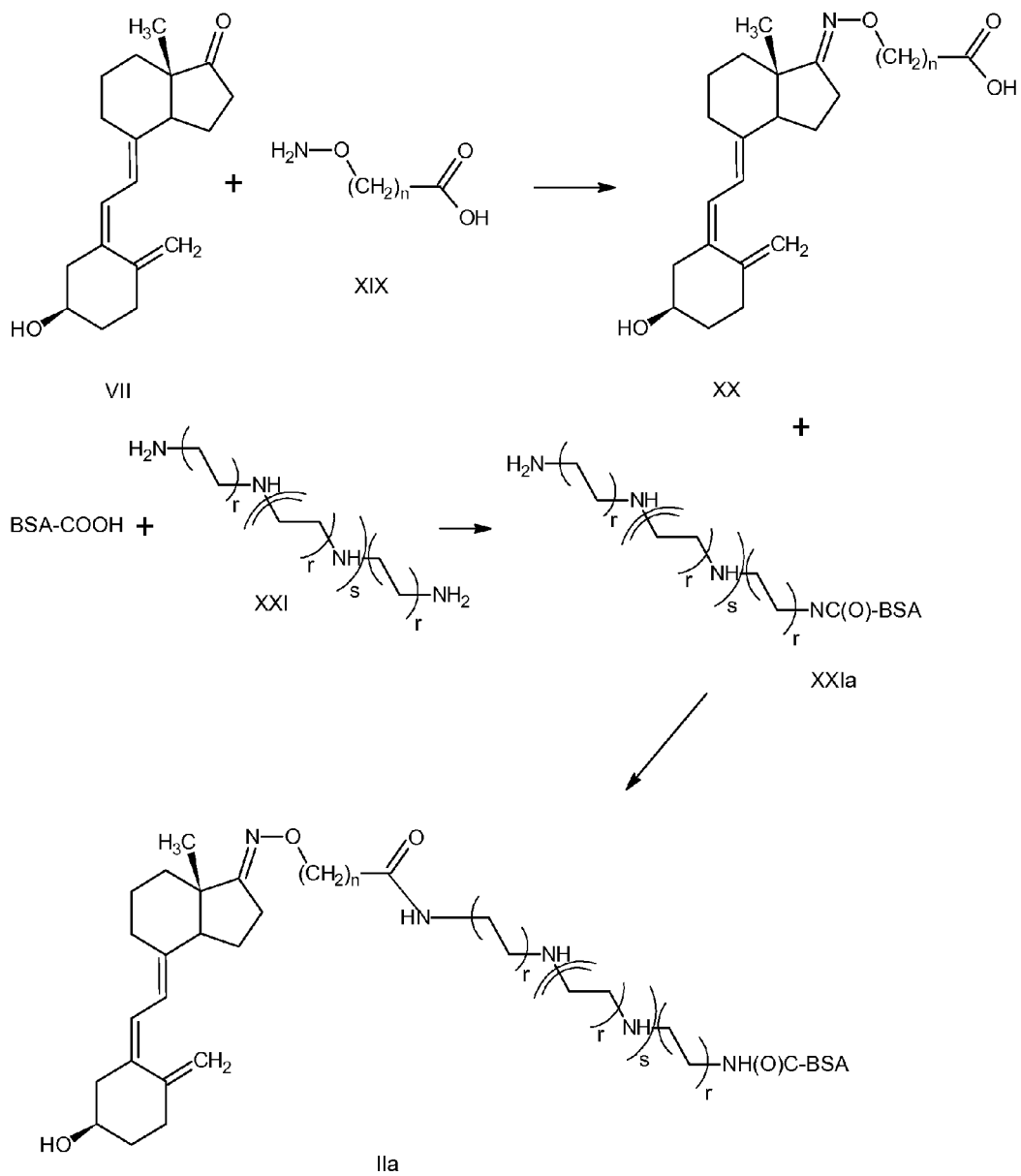
FIG. 3 is a schematic diagram of a synthesis of compounds in accordance with examples in accordance with the principles described herein.

FIG. 3 depicts, by way of illustration and not limitation, an example of a method of preparing a compound of the Formula IIa (where Z is BSA, by way of example and not limitation). Referring to FIG. 3, compound of Formula VII is reacted with aminooxyacetic acid (XIX) to form oxime of the Formula XX (2-((7aS,E)-4-((Z)-2-((R)-5-hydroxy-2-methylenecyclohexylidene)ethylidene)-7a-methyloctahydro-1H-inden-1-ylideneaminooxy)acetic acid). The reaction is carried out in an organic solvent such as, for example, an alcohol (e.g., methanol or ethanol), under conditions for forming an oxime. In some examples the temperature during the reaction is about 10° C. to about 30° C., or about 15° C. to about 25° C. The time period of the reaction is about 1 hour to about 30 hours, or about 2 hours to about 24 hours.

In a separate reaction, a poly(amino)acid immunogenic carrier (in this example, BSA (Z' of Formula II is BSA), by way of illustration and not limitation) is combined with a compound of the formula XXI to form a compound of the formula XXIa. The reaction is carried out in an aqueous buffered medium at a pH of about 5.0 to about 7.0, or about 5.5 to about 6.5, or about 6. An activation agent for facilitating the reaction of the carboxylic acid functionality of BSA with one or more of the amine group(s) of XXI is included in the reaction medium. Such coupling agents include, but are not limited to, 1-ethyl-3-(3-dimethylaminopropyl)-carbodiimide (EDAC), N-hydroxysuccinimide (NHS), or N,N,N',N'-tetramethyl-O—(N-succinimidyl)uronium tetrafluoroborate, or combinations of two or more of the above. The reaction is carried out under conditions for forming an amide. In some examples the temperature during the reaction is about 15° C. to about 25° C. The time period of the reaction is about 3 hours to about 24 hours, or about 4 hours to about 20 hours, or about 4 hours to about 10 hours, for example.

The compound of the Formula XX is treated with an activation agent such as, but are not limited to, 1-ethyl-3-(3-dimethylaminopropyl)carbodiimide (EDAC), N-hydroxysuccinimide (NHS), or N,N,N',N'-tetramethyl-O—(N-succinimidyl)uronium tetrafluoroborate, or combinations of two or more of the above, for example, to form activated XX. The reaction is carried out in a polar organic solvent such as, for example, an alkanol (e.g., methanol or ethanol), an ether (e.g., ethyl ether or tetrahydrofuran), a ketone (e.g., acetone), dimethylsulfoxide, acetonitrile, dichloromethane, or dimethylformamide (DMF), or a combination of two or more of the above, which may also contain water. In some examples the temperature during the reaction is about 15° C. to about 30° C., or about 20° C. to about 25° C., or about room temperature. The time period of the reaction is about 12 hours to about 36 hours, or about 20 to about 30 hours. The activated XX is reacted with the compound of the Formula XXIa to give a compound of the Formula IIa. As shown, $R^{1'}$ is the moiety of compound of the Formula IIa and $R^{1''}$ and $R^{1'''}$ are each H. However, consistent with the principles described herein, the resulting product may be a mixture of compounds wherein in one compound of the mixture $R^{1'}$ is the moiety of the compound of the Formula IIa, and in another compound of the mixture $R^{1'}$ and $R^{1''}$ are both the moiety of compound of the Formula IIa, and in another compound of the mixture $R^{1'}$ and $R^{1'''}$ are both the moiety of compound of the Formula IIa, and in another compound of the mixture all three of $R^{1'}$ and $R^{1''}$ and $R^{1'''}$ are the moiety of compound of the Formula IIa. The reaction is carried out in an organic solvent such as, for example, DMF or DMSO, for example, under conditions for forming an amide. In some examples the temperature during the reaction is about 15° C. to about 30° C., or about 20° C. to about 25° C., or room temperature. The time period of the reaction is about 12 hours to about 36 hours, or about 20 to about 30 hours.

Figure 4:
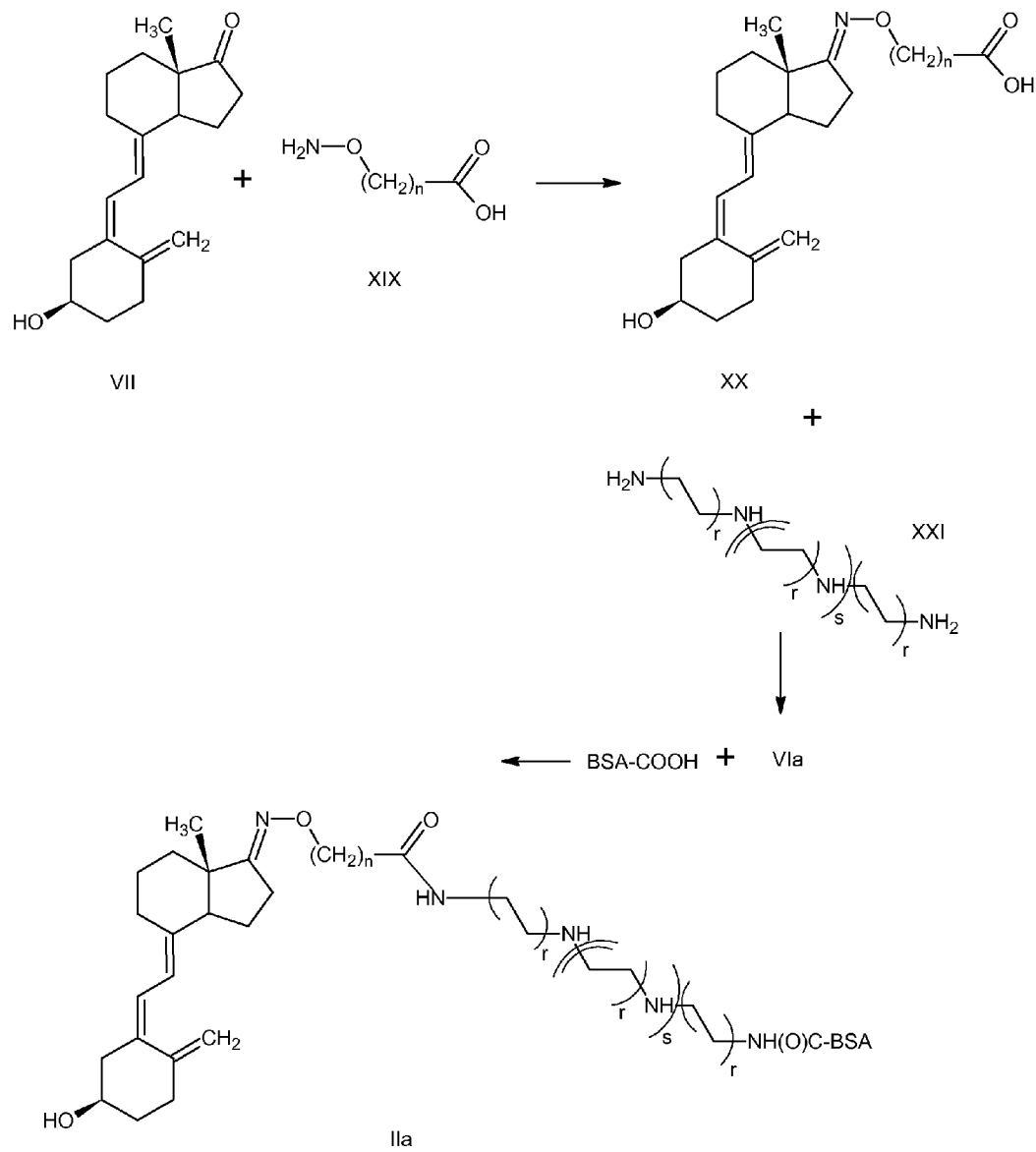
FIG. 4 is a schematic diagram of a synthesis of compounds in accordance with examples in accordance with the principles described herein.

FIG. 4 depicts, by way of illustration and not limitation, an alternate example of a method of preparing a compound of the Formula VIa and conversion of the compound of Formula VIa to a compound of the Formula IIa (where Z is BSA, by way of example and not limitation). Referring to FIG. 4, compound of Formula VII is reacted with aminooxyacetic acid (XIX) to form oxime of the Formula XX. The reaction is carried out in an organic solvent such as, for example, an alcohol (e.g., methanol or ethanol), under conditions for forming an oxime. In some examples the temperature during the reaction is about 10° C. to about 30° C., or about 15° C. to about 25° C. The time period of the reaction is about 1 hour to about 30 hours, or about 2 hours to about 24 hours.

Oxime of the Formula XX is combined with a compound of the formula XXI to form compound of the formula VIa. The reaction is carried out in an organic solvent such as, for example, an alkane (e.g., hexane or pentane), under conditions for forming an amide. In some examples the temperature during the reaction is about 15° C. to about 25° C. The time period of the reaction is about 10 hours to about 48 hours.

The compound of Formula VIa is reacted with a poly(amino)acid immunogenic carrier (Z' of Formula II is BSA, by way of illustration and not limitation) to give a compound of the Formula IIa. As shown, $R^{1'}$ is the moiety of compound of the Formula IIa and $R^{1''}$ and $R^{1'''}$ are each H. However, consistent with the principles described herein, the resulting product may be a mixture of compounds wherein in one compound of the mixture $R^{1'}$ is the moiety of the compound of the Formula IIa, and in another compound of the mixture $R^{1'}$ and $R^{1''}$ are both the moiety of compound of the Formula IIa, and in another compound of the mixture $R^{1'}$ and $R^{1'''}$ are both the moiety of compound of the Formula IIa, and in another compound of the mixture all three of $R^{1'}$ and $R^{1''}$ and $R^{1'''}$ are the moiety of compound of the Formula IIa. The reaction is carried out in an organic solvent such as, for example, an alkane (e.g., hexane or pentane), under conditions for forming an amide. In some examples the temperature during the reaction is about 15° C. to about 25° C. The time period of the reaction is about 10 hours to about 48 hours.

Figure 5:
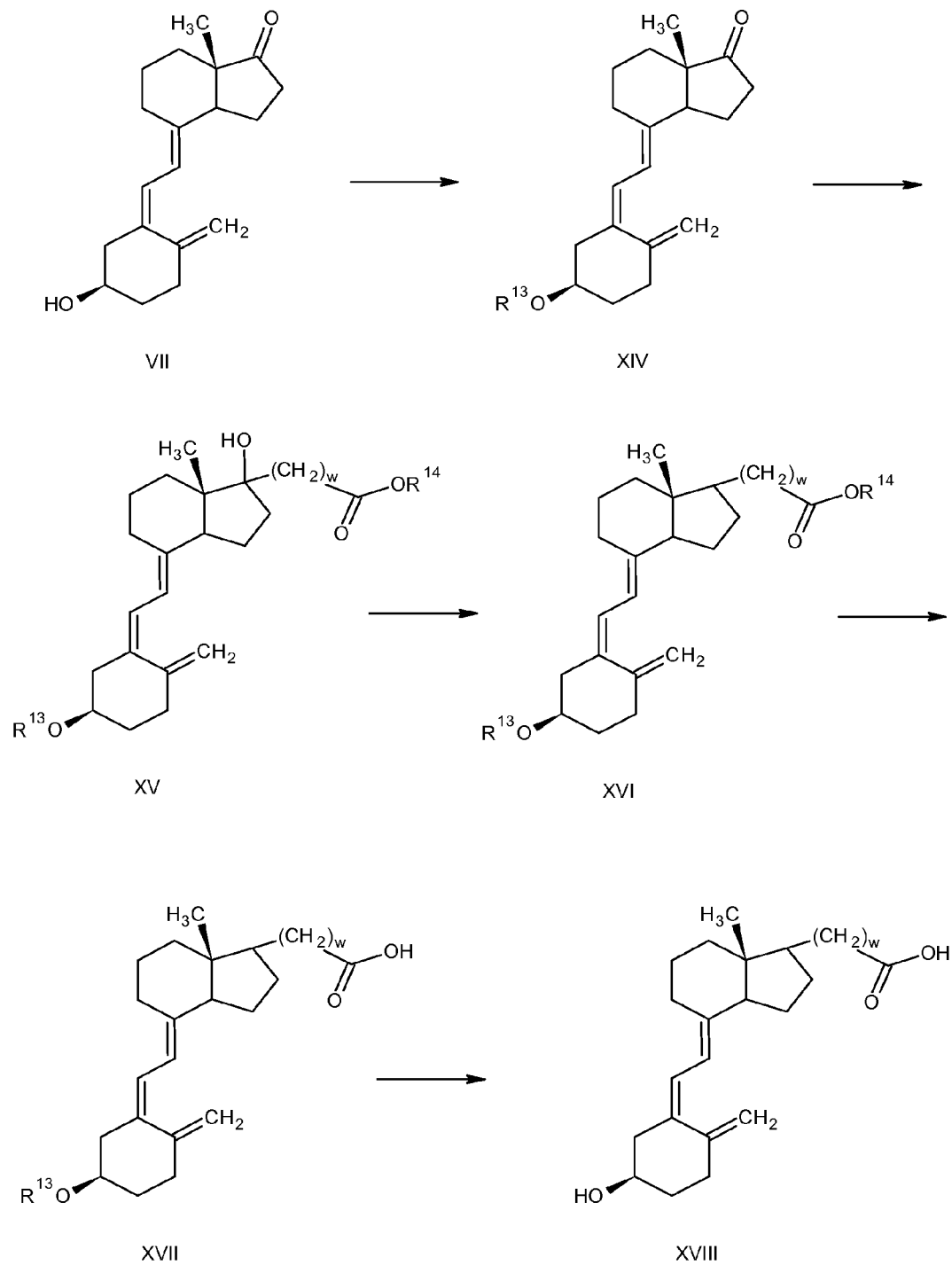
FIG. 5 is a schematic diagram of a synthesis of compounds in accordance with examples in accordance with the principles described herein.

Another example of a method of preparing examples of compounds in accordance with the principles described herein is described, by way of illustration and not limitation, with reference to FIG. 5. Other approaches may be employed to form the compounds consistent with the principles described herein. The preparation of a compound of Formula XVIII (Y is C in Formula I) is set forth in FIG. 5. Referring to FIG. 5, compound of the Formula VII (prepared, for example, as discussed in FIG. 3) is treated to protect the free hydroxyl group ($R^{13}$ is a protecting group) to form a compound of the Formula XIV. The conditions of the reaction are dependent on the nature of the protecting group, for example.

In one example, compound of the Formula VII is treated with tert-butyldimethylsilyl chloride under conditions for forming a silyl ether. The reaction is carried out in a polar organic solvent such as, for example, pyridine, dimethylsulfoxide, an ether (e.g., tetrahydrofuran, ethyl ether or 1,4-dioxane), acetonitrile, dichloromethane, or dimethylformamide (DMF). In some examples the temperature during the reaction is about 10° C. to about 30° C., or about 15° C. to about 25° C. The time period of the reaction is about 1 hour to about 30 hours, or about 2 hours to about 24 hours.

Examples of protecting groups, by way of example and not limitation, are silyl groups (such as, but not limited to, trimethylsilyl, trimethylsilyl, tert-butyldimethylsilyl, tri-isopropylsilyl, tert-butyldiphenylsilyl, for example), t-butoxycarbonyl (t-Boc), fluorenylmethyloxycarbonyl (Fmoc), acetaminomethyl (Acm), triphenyl methyl (Trt), benzyloxycarbonyl, biphenylisopropyloxycarbonyl, 1-amyloxycarbonyl, isobornyloxycarbonyl, alpha-dimethyl-3,5-dimethoxybenxyloxycarbonyl, o-nitrophenylsulfenyl, 2-cyano-1,1-dimentyl-ethoxycarbonyl, bromobenzyloxy, carbamyl, and formyl, for example.

A compound of the Formula XV is formed from the compound of Formula XIV by, for example, reaction with an alpha-haloester in the presence of zinc (Reformatsky reaction). In this example, the compound of Formula XIV is treated with a Reformatsky reagent such as, for example, $BrZnCH_2COOR^{14}$ (Zn and ethyl alpha-bromoacetate in the example shown, w=1) to give the compound of the Formula XV. The reaction is carried out in an organic solvent such as, for example, an ether (e.g., tetrahydrofuran or ethyl ether) or an aromatic solvent (e.g., benzene or toluene). In some examples the temperature during the reaction is about 4° C. to about 100° C., or about 10° C. to about 90° C. The time period of the reaction is about 4 hours to about 24 hours.

The free hydroxyl group of the compound of Formula XV is reduced to form a compound of the Formula XVI. The compound of Formula XV may be treated to reduce the hydroxy group by methods that include, but are not limited to, tosylate ester formation followed by treatment with a metal hydride such as, for example, $LiAlH_4$ or $NaBH_4$; removal of the hydroxyl to form an alkene (such as, for example, by treatment with a concentrated organic acid, e.g., concentrated sulfuric acid or concentrated hydrochloric acid) followed by hydrogenation in the presence of a catalyst such as, for example, platinum or palladium; for example. The conditions for the reaction depend on one or both of the nature of the reagents employed and the nature of the solvent, for example.

The resulting compound of the Formula XVI is treated to hydrolyze the ester group to a carboxylic acid group (de-esterification reaction) to give the compound of the Formula XVII. Numerous approaches are available for de-esterification and include, but are not limited to, saponification or treatment with an aqueous base such as, for example, NaOH or KOH with heat; or acid hydrolysis or treatment with an aqueous acid such as, for example, an aqueous mineral acid (such as, for example, hydrochloric acid or sulfuric acid), for example. The conditions for the reaction are dependent on one or more of the nature of the reagents and the nature of the ester, for example.

A compound of the Formula XVIII is formed by removal of protecting group $R^{13}$ from the compound of Formula XVII. Various approaches may be employed for removal of protecting groups and include, but are not limited to, treatment with dilute mineral acid (such as, for example, hydrochloric acid or sulfuric acid; treatment with an organic acid (such as, for example, acetic acid, in a polar organic solvent (such as, for example, an alkanol (e.g., methanol or ethanol), an ether (e.g., ethyl ether or tetrahydrofuran), a ketone (e.g., acetone), dimethylsulfoxide, acetonitrile, dichloromethane, or dimethylformamide (DMF), or a combination of two or more of the above, which may also contain water, under conditions for removing the protecting group to yield the compound of Formula XVIII. The conditions for the reaction are dependent on one or more of the nature of the reagents and the nature of the protecting group, for example.

Figure 6:
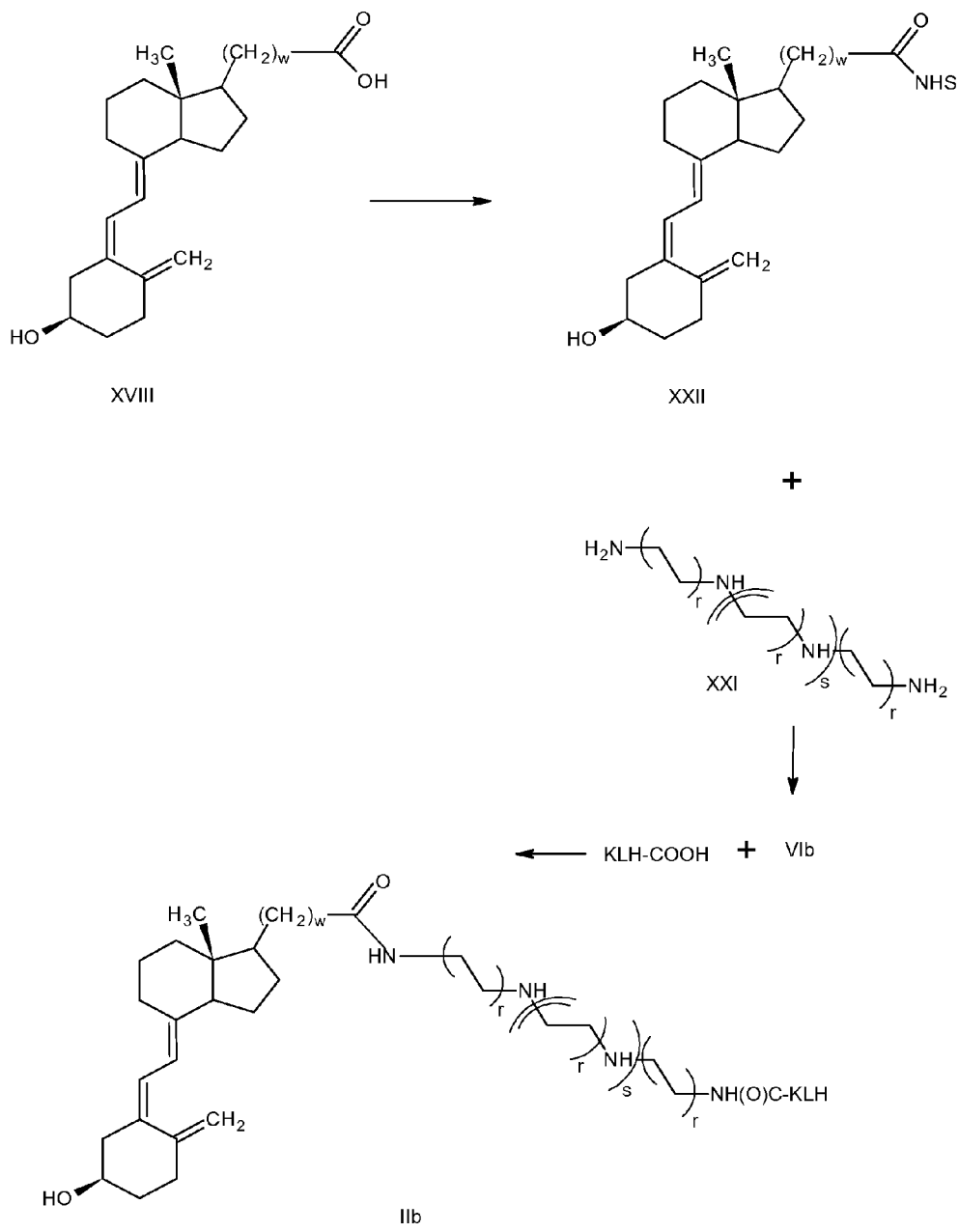
FIG. 6 is a schematic diagram of a synthesis of compounds in accordance with examples in accordance with the principles described herein.

FIG. 6 depicts, by way of illustration and not limitation, an example of a method of preparing a compound of the Formula VIb and conversion of the compound of Formula VIb to a compound of the Formula IIb (where Z' is KLH, by way of example and not limitation). Referring to FIG. 6, compound of Formula XVIII is treated to activate the carboxylic acid group such as, but not limited to, reaction to form an N-hydroxysuccinimide (NHS) ester (compound of the Formula XXII). The reaction is carried out in a polar organic solvent such as, for example, dimethylsulfoxide, an ether (e.g., tetrahydrofuran or ethyl ether), acetonitrile, dichloromethane, or dimethylformamide (DMF), for example, under conditions for forming an NHS ester. In some examples the temperature during the reaction is about 15° C. to about 25° C. The time period of the reaction is about 4 hours to about 48 hours.

NHS ester of the Formula XXII is combined with a compound of the formula XXI to form compound of the formula VIb. The reaction is carried out in an organic solvent such as, for example, an alkane (e.g., hexane or pentane), for example, under conditions for forming an amide. In some examples the temperature during the reaction is about 15° C. to about 25° C. The time period of the reaction is about 4 hours to about 48 hours.

The compound of Formula VIb is reacted with a poly(amino)acid immunogenic carrier (Z' of Formula II is KLH, for example) to give a compound of the formula IIb. As shown, $R^{1'}$ is the moiety of compound of the Formula IIb and $R^{1''}$ and $R^{1'''}$ are each H. However, consistent with the principles described herein, the resulting product may be a mixture of compounds wherein in one compound of the mixture $R^{1'}$ is the moiety of the compound of the Formula IIa, and in another compound of the mixture $R^{1'}$ and $R^{1''}$ are both the moiety of compound of the Formula IIa, and in another compound of the mixture $R^{1'}$ and $R^{1'''}$ are both the moiety of compound of the Formula IIa, and in another compound of the mixture all three of $R^{1'}$ and $R^{1''}$ and $R^{1'''}$ are the moiety of compound of the Formula IIb. The reaction is carried out in an organic solvent such as, for example, an alkane (e.g., hexane or pentane), under conditions for forming an amide. In some examples the temperature during the reaction is about 15° C. to about 25° C. The time period of the reaction is about 4 hours to about 48 hours.

In an alternate route, a compound of the Formula IIb may be prepared from a compound of the Formula XVIII in a manner similar to that described above for FIG. 3 for the preparation of the compound of the Formula IIa.

Figure 7:
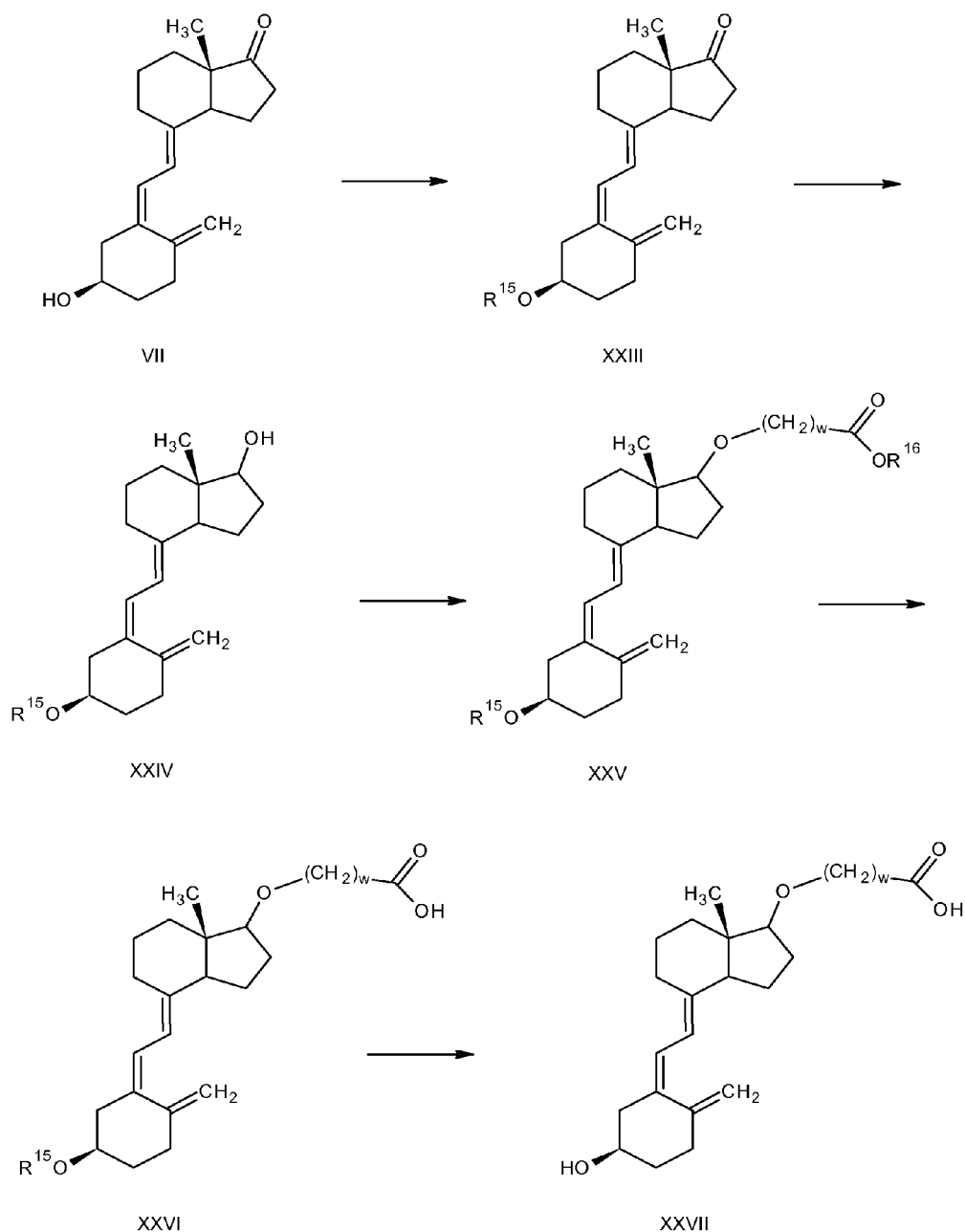
FIG. 7 is a schematic diagram of a synthesis of compounds in accordance with examples in accordance with the principles described herein.

Another example of a method of preparing examples of compounds in accordance with the principles described herein is described, by way of illustration and not limitation, with reference to FIG. 7. Other approaches may be employed to form the compounds consistent with the principles described herein. The preparation of a compound of Formula XXVII (Y is O in Formula I and w is 0 to 10 or 1 to 10) is set forth in FIG. 7. Referring to FIG. 7, compound of the Formula VII (prepared, for example, as discussed in FIG. 2) is treated to protect the free hydroxyl group ($R^{15}$ is a protecting group) to form a compound of the Formula XXIII. The conditions of the reaction are dependent on the nature of the protecting group, for example.

In one example, compound of the Formula VII is treated with tert-butyldimethylsilyl chloride (by way of example and not limitation) under conditions for forming a silyl ether. The reaction is carried out in a polar organic solvent such as, for example, pyridine, dimethylsulfoxide, an ether (e.g., tetrahydrofuran, ethyl ether, or 1,4-dioxane), acetonitrile, dichloromethane, or dimethylformamide (DMF). In some examples the temperature during the reaction is about 15° C. to about 25° C. The time period of the reaction is about 4 hours to about 48 hours.

A compound of the Formula XXIV is formed from the compound of Formula XXIII by reduction of the ketone group to a hydroxy group, for example. The compound of Formula XXIII may be treated to reduce the hydroxy group by methods that include, but are not limited to, treatment with a metal hydride such as, for example, $LiAlH_4$ or $NaBH_4$, to give the compound of the Formula XXIV. The reaction is carried out in an organic solvent such as, for example, an alkanol (e.g., ethanol). In some examples the temperature during the reaction is about 0° C. to about 25° C. The time period of the reaction is about 0.5 hours to about 4 hours.

A compound of the Formula XXV is formed from the compound of Formula XXIV by, for example, reaction with a halo ester (such as, by way of example and not limitation) an alpha-haloester in the presence of a base. In this example, the compound of Formula XXV is treated with, for example, $BrCH_2COOR^{16}$ (ethyl alpha-bromoacetate in the example shown, w is 1 and $R^{16}$ is ethyl) to give the compound of the Formula XXV. The reaction is carried out by forming an alkoxide ion from the hydroxy group of the compound of the Formula XXIV in the presence of a base such as, for example, KOH, NaOH, $Na_2CO_3$, or $K_2CO_3$, and reaction of the alkoxide with the haloester. The solvent for the reaction is an aqueous solvent, which may contain 1% to 40% of a polar organic solvent such as described above. In some examples the temperature during the reaction is about 50° C. to about 100° C., or about 50° C. to about 90° C., for example. The time period of the reaction is about 0.5 hours to about 24 hours, or about 1 hour to about 8 hours, for example.

The resulting compound of the Formula XXV is treated to hydrolyze the ester group to a carboxylic acid group (de-esterification reaction) to give the compound of the Formula XXVI. Numerous approaches are available for de-esterification and include, but are not limited to, saponification or treatment with an aqueous base such as, for example, NaOH or KOH, with heat; acid hydrolysis or treatment with an aqueous acid such as, for example, an aqueous mineral acid (such as, for example, hydrochloric acid, or sulfuric acid, for example. The conditions for the reaction are dependent on one or more of the nature of the reagents and the nature of the ester, for example.

A compound of the Formula XXVII is formed by removal of protecting group $R^{15}$ from the compound of Formula XXVI. Various approaches may be employed for removal of protecting groups and include, but are not limited to, treatment with dilute mineral acid (such as, for example, hydrochloric acid or sulfuric acid); treatment with an organic acid (such as, for example, acetic acid), in a polar organic solvent (such as, for example, an alkanol (e.g., methanol or ethanol), an ether (e.g., ethyl ether, tetrahydrofuran, or 1,4-dioxane), a ketone (e.g., acetone), dimethylsulfoxide, acetonitrile, dichloromethane, dimethylformamide (DMF), or a combination of two or more of the above, which may also contain water, under conditions for removing the protecting group to yield the compound of Formula XXVII. The conditions for the reaction are dependent on one or more of the nature of the reagents and the nature of the protecting group, for example.

Figure 8:
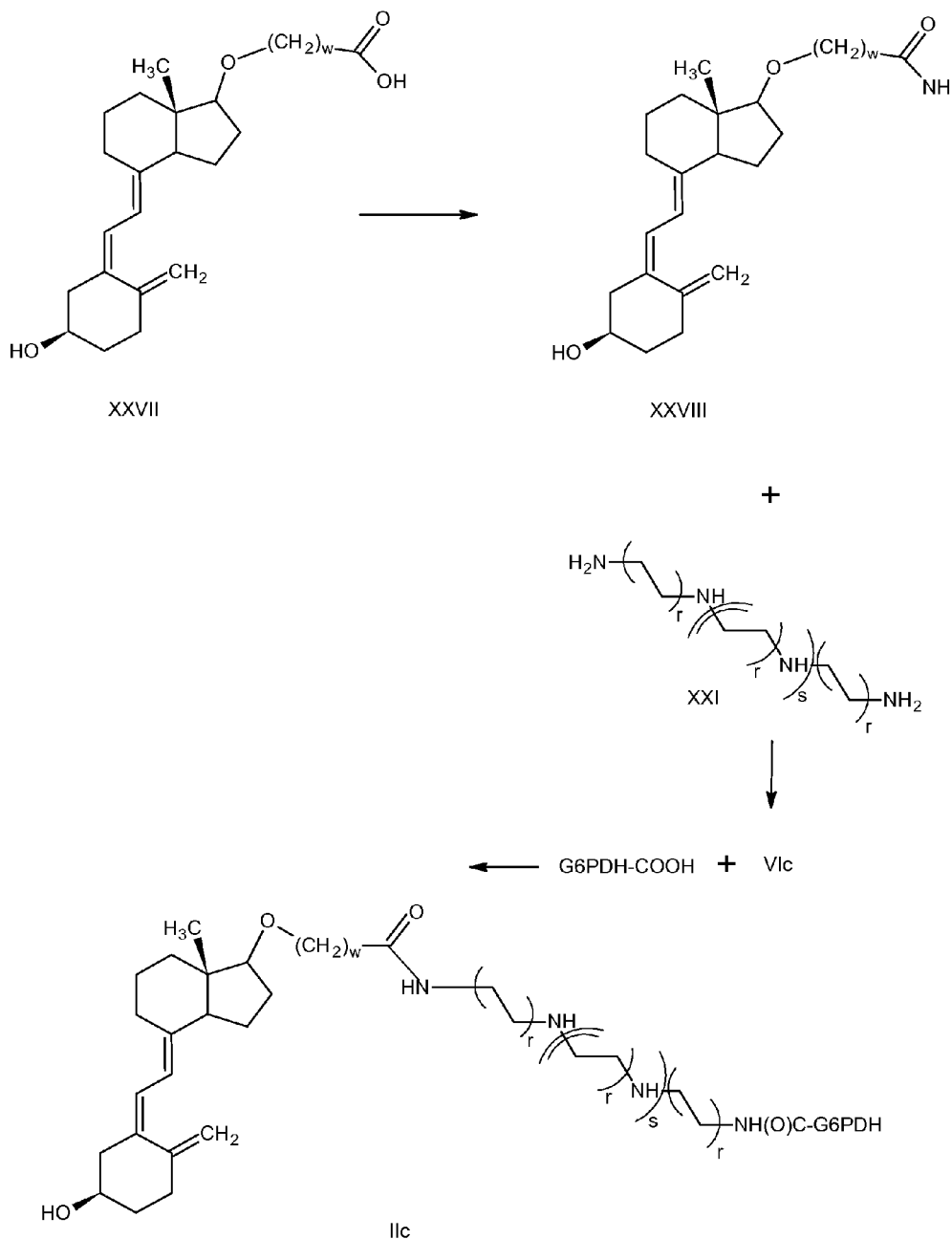
FIG. 8 is a schematic diagram of a synthesis of compounds in accordance with examples in accordance with the principles described herein.

FIG. 8 depicts, by way of illustration and not limitation, an example of a method of preparing a compound of the Formula VIc and conversion of the compound of Formula VIc to a compound of the Formula IIc (where Z' is the enzyme G6PDH, by way of example and not limitation). Referring to FIG. 8, compound of Formula XXVII is treated to activate the carboxylic acid group such as, but not limited to, reaction to form an N-hydroxysuccinimide (NHS) ester (compound of the Formula XXVIII). The reaction is carried out in a polar organic solvent such as, for example, dimethylsulfoxide, an ether (e.g., tetrahydrofuran, ethyl ether, or 1,4-dioxane), acetonitrile, dichloromethane, or dimethylformamide (DMF), for example, under conditions for forming an NHS ester. In some examples the temperature during the reaction is about 15° C. to about 25° C. The time period of the reaction is about 1 hour to about 24 hours.

NHS ester of the Formula XXVIII is combined with a compound of the Formula XXI to form compound of the formula VIc. The reaction is carried out in an organic solvent such as, for example, an alkane (e.g., hexane or pentane), for example, under conditions for forming an amide. In some examples the temperature during the reaction is about 15° C. to about 25° C. The time period of the reaction is about 1 hour to about 24 hours.

The compound of Formula VIc is reacted with the enzyme, G6PDH (Z' of Formula II is G6PDH, for example), to give a compound of the Formula IIc. As shown, $R^{1'}$ is the moiety of compound of the Formula IIc and $R^{1''}$ and $R^{1'''}$ are each H. However, consistent with the principles described herein, the resulting product may be a mixture of compounds wherein in one compound of the mixture $R^{1'}$ is the moiety of the compound of the Formula IIa, and in another compound of the mixture $R^{1'}$ and $R^{1''}$ are both the moiety of compound of the Formula IIa, and in another compound of the mixture $R^{1'}$ and $R^{1'''}$ are both the moiety of compound of the Formula IIa, and in another compound of the mixture all three of $R^{1'}$ and $R^{1''}$ and $R^{1'''}$ are the moiety of compound of the Formula IIc. The reaction is carried out in an organic solvent such as, for example, an alkane (e.g., hexane or pentane), under conditions for forming an amide. In some examples the temperature during the reaction is about 15° C. to about 25° C. The time period of the reaction is about 1 hour to about 24 hours.

In an alternate route, a compound of the Formula IIc may be prepared from a compound of the Formula XXVII in a manner similar to that described above for FIG. 3 for the preparation of the compound of the Formula IIa.

Other compounds in accordance with the principles described herein may be prepared in a manner similar to that described above.

Preparation of Binding Partners

Examples of compounds in accordance with the principles described herein where Z is a poly(amino acid) immunogenic carrier or a non-poly(amino acid) immunogenic carrier may be employed to prepare binding partners for vitamin D such as, for example, aptamers for vitamin D or antibodies for vitamin D, which include, but are not limited to, antibodies specific for vitamin $D_3$, antibodies specific for vitamin $D_2$, antibodies specific for 25-hydroxyvitamin $D_3$, antibodies specific for 25-hydroxyvitamin $D_2$, antibodies specific for 3-epi-25-hydroxyvitamin $D_3$, and antibodies specific for 3-epi-25-hydroxyvitamin $D_2$, for example. Of particular interest are antibodies specific for 3-epi-25-hydroxyvitamin $D_3$, antibodies specific for 3-epi-25-hydroxyvitamin $D_2$, and antibodies specific for epimers of other vitamin D compounds ("antibodies for epimeric vitamin D"), which can be employed in assays for 3-epi-25-hydroxyvitamin $D_3$ and for 3-epi-25-hydroxyvitamin $D_2$, or which can be employed in assays for non-epimeric vitamin D to reduce or eliminate interference from epimeric forms of vitamin D such as, for example, 3-epi-25-hydroxyvitamin $D_3$ and from 3-epi-25-hydroxyvitamin $D_2$, which may be present in a sample to be tested for the presence of vitamin D.

Antibodies may be a monoclonal antibodies or a polyclonal antibodies and may include a complete immunoglobulin or fragment thereof, which immunoglobulins include, but are not limited to, various classes and isotypes, such as IgA, IgD, IgE, IgG and IgM, for example. Fragments thereof may include Fab, Fv and $F(ab')_2$, Fab', and the like. In addition, aggregates, polymers, and conjugates of immunoglobulins or their fragments can be used where appropriate so long as binding affinity for a particular molecule is maintained.

Antibodies in accordance with the principles described herein may be prepared by techniques including, but not limited to, immunization of a host and collection of sera (polyclonal), preparing continuous hybrid cell lines and collecting the secreted protein (monoclonal) or cloning and expressing nucleotide sequences or mutagenized versions thereof coding at least for the amino acid sequences required for specific binding of natural antibodies, for example.

Monoclonal antibodies can be prepared by techniques such as preparing continuous hybrid cell lines and collecting the secreted protein (somatic cell hybridization techniques). Monoclonal antibodies may be produced according to the standard techniques of Köhler and Milstein, *Nature* 265: 495-497, 1975. Reviews of monoclonal antibody techniques are found in Lymphocyte Hybridomas, ed. Melchers, et al. Springer-Verlag (New York 1978), Nature 266: 495 (1977), Science 208: 692 (1980), and Methods of Enzymology 73 (Part B): 3-46 (1981).

In another approach for the preparation of antibodies, the sequence coding for antibody binding sites can be excised from the chromosome DNA and inserted into a cloning vector, which can be expressed in bacteria to produce recombinant proteins having the corresponding antibody binding sites. This approach involves cloning and expressing nucleotide sequences or mutagenized versions thereof coding at least for the amino acid sequences required for specific binding of natural antibodies.

In one approach for the production of monoclonal antibodies, a first step includes immunization of an antibody-producing animal such as a mouse, a rat, a goat, a sheep, or a cow with an immunogen that comprises a compound of Formula I wherein Z is an immunogenic carrier, for example. Immunization can be performed with or without an adjuvant such as complete Freund's adjuvant or other adjuvants such as monophosphoryl lipid A and synthetic trehalose dicorynomycolate adjuvant. A next step includes isolating spleen cells from the antibody-producing animal and fusing the antibody-producing spleen cells with an appropriate fusion partner, typically a myeloma cell, such as by the use of polyethylene glycol or other techniques. Typically, the myeloma cells used are those that grow normally in hypoxanthine-thymidine (HT) medium but cannot grow in hypoxanthine-aminopterin-thymidine (HAT) medium, used for selection of the fused cells. A next step includes selection of the fused cells, typically by selection in HAT medium. A next step includes screening the cloned hybrids for appropriate antibody production using immunoassays such as, for example, an enzyme-linked immunosorbent assay (ELISA) or other immunoassays appropriate for screening.

An antibody (prepared from an immunogen in accordance with the principles described herein) with the requisite specificity may be selected by screening methodologies, which include, by way of illustration and not limitation, ELISA, dot blots, Western analysis, and Surface Plasmon Resonance, for example. In this manner an antibody is obtained that binds to a vitamin D analyte of interest and does not bind to any detectable degree to a vitamin D molecule that is not of interest in a particular assay. In some examples in accordance with the principles described herein, an antibody that binds to a vitamin D analyte of interest has a binding affinity for the vitamin D analyte of interest of about $10^7$ to about $10^{14}$ liters/mole, or about $10^7$ to about $10^{11}$ liters/mole, or about $10^7$ to about $10^{12}$ liters/mole, or about $10^8$ to about $10^{14}$ liters/mole, or about $10^8$ to about $10^{11}$ liters/mole, or about $10^8$ to about $10^{12}$ liters/mole, for example. The phrase "any detectable degree" means that the antibody that specifically binds to a vitamin D analyte of interest (e.g., 3-3pi-25-hydroxyvitamin D) has a binding affinity for a vitamin D molecule that is not of interest (e.g., a non-epi-vitamin D compound) of less than about $10^4$ liters/mole, or less than about $10^3$ liters/mole, or less than about $10^2$ liters/mole, or less than about 10 liters/mole, for example.

In one example in accordance with the principles described herein, an immunogen, prepared from a compound of Formula I above wherein Z is an immunogenic carrier, is employed to prepare antibodies that are specific for 3-epi-25-hydroxyvitamin $D_3$ where the antibodies do not bind to any detectable degree with 25-hydroxyvitamin $D_3$ or to other variants of vitamin D including non-epi-vitamin D compounds such as, for example, 25-hydroxyvitamin D; calcidiol; 1,25-dihydroxyvitamin $D_3$; 1,25-dihydroxy vitamin $D_4$; 1,25-dihydroxy vitamin $D_5$; and 1,25-dihydroxy vitamin $D_6$, for example.

In another example in accordance with the principles described herein, an immunogen, prepared from a compound of Formula I above wherein Z is an immunogenic carrier, is employed to prepare antibodies that are specific for 3-epi-25-hydroxyvitamin $D_2$ where the antibodies do not bind to any detectable degree with 25-hydroxyvitamin $D_2$ or to other variants of vitamin D including non-epi-vitamin D compounds such as, for example, 25-hydroxyvitamin D; calcidiol; 1,25-dihydroxyvitamin $D_3$; 1,25-dihydroxy vitamin $D_4$; 1,25-dihydroxy vitamin $D_5$; and 1,25-dihydroxy vitamin $D_6$, for example.

In one example, by way of illustration and not limitation, an immunogen is employed wherein Z in the compound of Formula I is BSA. This immunogen is used to immunize mice (e.g., BALB/c mice, Swiss Webster mice or an AJ strain of mice) intraperitoneally. Serum samples from these mice are tested for anti-3-epi-25-hydroxyvitamin $D_3$ antibodies using a conjugate of 3-epi-25-hydroxyvitamin $D_3$ and ovalbumin (ovalbumin conjugate). A microtiter plate ELISA is employed and the antibodies are examined for binding to the ovalbumin conjugate and subsequently to 3-epi-25-hydroxyvitamin $D_3$. Mice with highest titers are boosted three days prior to fusion. On the day of fusion, spleen cells are harvested from these mice and are fused with myeloma cell line P3X63Ag8.653 using PEG assisted fusion protocols. After about ten days, hybridomas supernatants are screened for anti-3-epi-25-hydroxyvitamin $D_3$ antibodies using a plate ELISA. Positive clones are further expanded, sub-cloned and supernatants are purified using a protein A sepharose column. Purified antibody samples are tested using ELISA for binding to the ovalbumin conjugate and to free 3-epi-25-hydroxyvitamin $D_3$.

Particular examples, by way of illustration and not limitation, of antibodies prepared as described above that are specific for 3-epi-25-hydroxyvitamin $D_3$ or specific for 3-epi-25-hydroxyvitamin $D_2$, include antibody 4G8 and antibody 8F10, for example.

In some examples, antibodies in accordance with the principles described herein may be employed to purify vitamin D compounds. For example, antibodies such as those described above may be bound to a support and the support employed to purify vitamin D compounds. In one example, antibodies for 3-epi-25-hydroxyvitamin $D_3$ may be bound to an affinity purification chromatography substrate such as, for example, a column, and vitamin D preparations may be contacted with the chromatography substrate where antibody on the substrate binds 3-epi-25-hydroxyvitamin $D_3$ from the vitamin D preparation while other vitamin D compounds are eluted from the substrate.

General Description of Assays for Vitamin D

Some examples in accordance with the principles described herein are directed to methods of determining one or both of the presence and the amount of a vitamin D analyte in a sample suspected of containing the vitamin D analyte and may be referred to herein as "assays for vitamin D."

The phrase "vitamin D" refers to one or more of 25-hydroxyvitamin D; calcidiol; 1,25-dihydroxy vitamin $D_2$; 1,25-dihydroxyvitamin $D_3$; 1,25-dihydroxy vitamin $D_4$; 1,25-dihydroxy vitamin $D_5$; and 1,25-dihydroxy vitamin $D_6$; including epimeric forms and metabolites of all of the above. Thus, vitamin D analyte includes vitamin D and epimers of vitamin D as defined above. Some examples in accordance with the principles described herein are directed to methods of determining one or both of the presence and the amount of epimeric forms of vitamin D in a sample suspected of containing epimeric forms of vitamin D (such as, for example, 3-epi-25-hydroxyvitamin $D_3$ or 3-epi-25-hydroxyvitamin $D_2$) and may be referred to herein as "assays for epimers of vitamin D."

In one example of a method for determining a vitamin D analyte, by way of illustration and not limitation, a combination is provided that comprises the sample, an antibody for an epimer of vitamin D produced in accordance with the principles described herein and a conjugate comprising a vitamin D analog and a member of a signal producing system.

As mentioned above, the sample and reagents are provided "in combination in the medium." While the order of addition to the medium may be varied to form the combination, there will be certain preferences for some embodiments of the assay formats described herein. In one example, by way of illustration and not limitation, the order of addition is to add all the materials simultaneously and determine the effect that the assay medium has on the signal as in a homogeneous assay. In another example, by way of illustration and not limitation, each of the reagents, or groups of reagents, can be combined sequentially. In some embodiments, an incubation step may be involved subsequent to each addition as discussed above. In heterogeneous assays, separation and washing steps may also be employed after one or more incubation steps.

The phrase "vitamin D analog" refers to a compound that competes with a vitamin D analyte for a receptor such as an antibody for vitamin D or an antibody for an epimer of vitamin D. The vitamin D analog may be a modified vitamin D where the modification provides means to join vitamin D to another molecule such as, but not limited to, a support, a label, a small molecule, or a binding partner for a small molecule, for example. The vitamin D analog may be linked to another molecule directly or indirectly by means of a linking group. The vitamin D analog may be, for example, a molecule structurally related to vitamin D or vitamin D conjugated to another molecule through a linking group. In some examples in accordance with the principles described herein, a vitamin D analog may be a compound of the Formula I wherein Z is poly(amino acid) label moiety or a non-poly(amino acid) label moiety or wherein Z is an immunogenic carrier where such compound of Formula I competes with a vitamin D analyte for binding to a vitamin D antibody.

The sample to be analyzed is one that is suspected of containing a vitamin D analyte. The samples may be biological samples or non-biological samples. Biological samples may be from a mammalian subject or a non-mammalian subject. Mammalian subjects may be, e.g., humans or other animal species. Biological samples include biological fluids such as whole blood, serum, plasma, sputum, lymphatic fluid, semen, vaginal mucus, feces, urine, spinal fluid, saliva, stool, cerebral spinal fluid, tears, mucus, and the like; biological tissue such as hair, skin, sections or excised tissues from organs or other body parts; and so forth. In many instances, the sample is whole blood, plasma or serum. Non-biological samples including, but not limited to, waste streams, for example, may also be analyzed using compounds in accordance with the principles described herein.

The sample can be prepared in any convenient medium, which may be, for example, an assay medium, which is discussed more fully hereinbelow. In some instances a pretreatment may be applied to the sample such as, for example, to lyse blood cells. In some examples, such pretreatment is performed in a medium that does not interfere subsequently with an assay.

The combination in the medium is subjected to conditions for binding of the vitamin D analyte and the vitamin D analog to the antibody for vitamin D analyte to form a complex. The amount of the complex is measured where the amount of the complex is related to one or both of the presence and amount of the vitamin D analyte in the sample.

An assay for a vitamin D analyte can be performed either without separation (homogeneous) or with separation (heterogeneous) of any of the assay components or products. Heterogeneous assays usually involve one or more separation steps and can be competitive or non-competitive. Immunoassays may involve labeled or non-labeled reagents. Immunoassays involving non-labeled reagents usually comprise the formation of relatively large complexes involving one or more antibodies prepared from immunogenic conjugates in accordance with the principles described herein. Such assays include, for example, immunoprecipitin and agglutination methods and corresponding light scattering techniques such as, e.g., nephelometry and turbidimetry, for the detection of antibody complexes. Labeled immunoassays include, but are not limited to, chemiluminescence immunoassays, enzyme immunoassays, fluorescence polarization immunoassays, radioimmunoassays, inhibition assays, induced luminescence assays, and fluorescent oxygen channeling assays, for example.

One general group of immunoassays includes immunoassays using a limited concentration of a compound in accordance with the principles described herein. Another group of immunoassays involves the use of an excess of one or more of the principal reagents such as, for example, an excess of a compound in accordance with the principles described herein. Another group of immunoassays includes separation-free homogeneous assays in which signal from a labeled vitamin D analog is modulated upon binding of the labeled vitamin D analog to an antibody produced in accordance with the principles described herein, thus competing with a vitamin D analyte that may be present in the sample.

As mentioned above, the assays can be performed either without separation (homogeneous) or with separation (heterogeneous) of any of the assay components or products. Homogeneous immunoassays are exemplified by the EMIT® assay (Siemens Healthcare Diagnostics Inc., Deerfield, Ill.) disclosed in Rubenstein, et al., U.S. Pat. No. 3,817,837, column 3, line 6 to column 6, line 64; immunofluorescence methods such as those disclosed in Ullman, et al., U.S. Pat. No. 3,996,345, column 17, line 59, to column 23, line 25; enzyme channeling immunoassays ("ECIA") such as those disclosed in Maggio, et al., U.S. Pat. No. 4,233,402, column 6, line 25 to column 9, line 63; the fluorescence polarization immunoassay ("FPIA") as disclosed, for example, in, among others, U.S. Pat. No. 5,354,693; and enzyme immunoassays such as the enzyme linked immunosorbant assay ("ELISA"). Exemplary of heterogeneous assays are the radioimmunoassay, disclosed in Yalow, et al., J. Clin. Invest. 39:1157 (1960). The relevant portions of the above disclosures are all incorporated herein by reference.

Other enzyme immunoassays are the enzyme modulate mediated immunoassay ("EMMIA") discussed by Ngo and Lenhoff, FEBS Lett. (1980) 116:285-288; the substrate labeled fluorescence immunoassay ("SLFIA") disclosed by Oellerich, J. Clin. Chem. Clin. Biochem. (1984) 22:895-904; the combined enzyme donor immunoassays ("CEDIA") disclosed by Khanna, et al., Clin. Chem. Acta (1989) 185:231-240; homogeneous particle labeled immunoassays such as particle enhanced turbidimetric inhibition immunoassays ("PETINIA"), particle enhanced turbidimetric immunoassay ("PETIA"); the Affinity Chromium dioxide Mediated Immuno Assay ("ACMIA") assay format, which is described in U.S. Pat. Nos. 7,186,518, 5,147,529, 5,128,103, 5,158,871, 4,661,408, 5,151,348, 5,302,532, 5,422,284, 5,447,870, and 5,434,051, the disclosures of which are incorporated herein in their entirety; for example.

Other assays include acridinium ester label assays such as those discussed in U.S. Pat. Nos. 6,355,803; 6,673,560; 7,097,995 and 7,319,041, the relevant disclosures of which are incorporated herein by reference. A particular example of an acridinium ester label assay is an acridinium ester label immunoassay using paramagnetic particles as a solid phase ("ADVIA" immunoassay). Other assays include the sol particle immunoassay ("SPIA"), the disperse dye immunoassay ("DIA"); the metalloimmunoassay ("MIA"); the enzyme membrane immunoassays ("EMIA"); and luminoimmunoassays ("LIA"). Other types of assays include immunosensor assays involving the monitoring of the changes in the optical, acoustic and electrical properties of the present conjugate upon the binding of vitamin D analyte. Such assays include, for example, optical immunosensor assays, acoustic immunosensor assays, semiconductor immunosensor assays, electrochemical transducer immunosensor assays, potentiometric immunosensor assays, amperometric electrode assays.

Heterogeneous assays usually involve one or more separation steps and can be competitive or non-competitive. A variety of competitive and non-competitive heterogeneous assay formats are disclosed in Davalian, et al., U.S. Pat. No. 5,089,390, column 14, line 25 to column 15, line 9, incorporated herein by reference. In an example of a competitive heterogeneous assay, a support having an antibody for a vitamin D analyte bound thereto is contacted with a medium containing the sample suspected of containing the vitamin D analyte and a labeled compound in accordance with the principles described herein. Vitamin D analyte in the sample competes, for binding to the antibody for the vitamin D analyte, with a vitamin D analog bearing a detectable label. After separating the support and the medium, the label activity of the support or the medium is determined by conventional techniques and is related to the amount of vitamin D analyte in the sample. In a variation of the above competitive heterogeneous assay, the support comprises a vitamin D analog as the labeled reagent and vitamin D antibody comprises a label.

In some examples, a sample to be analyzed is combined in an assay medium with an antibody for the vitamin D analyte and labeled vitamin D analog. The medium is examined for one or both of the presence and amount of a complex comprising the labeled vitamin D analog and the antibody for the vitamin D analyte where the presence and/or the amount of such complex indicates the presence and/or amount of the vitamin D analyte in the sample.

In some examples in accordance with the principles described herein, the sample to be analyzed is subjected to a pretreatment to release the vitamin D analyte from endogenous binding substances such as, for example, plasma or serum proteins that bind vitamin D. The release of the vitamin D analyte from endogenous binding substances may be carried out, for example, by addition of a digestion agent or a releasing agent or a combination of a digestion agent and a releasing agent used sequentially. The digestion agent is one that breaks down the endogenous binding substances so that they can no longer bind vitamin D. Such agents include, but are not limited to, proteinase K and proteinase K and protein denaturing agents such as, e.g., detergents (sodium dodecyl sulfate, for example). Releasing agents for releasing vitamin D from endogenous binding substances include, by way of illustration and not limitation, acidic denaturing agents such as, for example, salicylic acid, warfarin, sulfonic acids, toluene sulfonic acids, naphthalene sulfonic acid, anilinonaphthalene sulfonic acids (ANS) (including, e.g., 1-anilinonaphthalene-8-sulfonic acid (1,8-ANS) and 8-anilinonapthalene-1-sulfonic acid (8-ANS)), salicylic acids and derivatives of the above.

The conditions such as, for example, duration, temperature, pH and concentration of the releasing agent in the medium for carrying out the digestion or releasing actions are dependent on the nature of the endogenous binding substances, the nature of the sample, and the nature of the releasing agent, for example. In general, the conditions are sufficient to achieve the desired effect or function. In some examples in accordance with the principles described herein, an effective concentration of releasing agent is about 0.01 to about 20 mg/mL, or about 0.01 to about 10 mg/mL, or about 0.01 to about 5 mg/mL, or about 0.1 to about 20 mg/mL, or about 0.1 to about 10 mg/mL, or about 0.1 to about 5 mg/mL, or about 0.1 to about 1 mg/mL. The pretreatment of the sample to release the vitamin D analyte from endogenous binding substances may be carried out as a separate step prior to conducting an assay or as a first step in an assay. In either case, one or more reagents may be required to stop the action of the digestion agent and/or the releasing agent.

The conditions for conducting the assays include carrying out the assay in an aqueous buffered medium at a moderate pH, generally that which provides optimum assay sensitivity. The aqueous medium may be solely water or may include from 0.1 to about 40 volume percent of a cosolvent. The pH for the medium will be in the range of about 4 to about 11, or in the range of about 5 to about 10, or in the range of about 6.5 to about 9.5, for example. The pH will usually be a compromise between optimum binding of the binding members of any specific binding pairs, the pH optimum for other reagents of the assay such as members of the signal producing system, and so forth. Various buffers may be used to achieve the desired pH and maintain the pH during the assay. Illustrative buffers include, by way of illustration and not limitation, borate, phosphate, carbonate, TRIS, barbital, PIPES, HEPES, MES, ACES, MOPS, and BICINE, for example. The particular buffer employed is not critical, but in an individual assay one or another buffer may be preferred.

Various ancillary materials may be employed in the assay methods. For example, in addition to buffers the medium may comprise stabilizers for the medium and for the reagents employed. In some embodiments, in addition to these additives, proteins may be included, such as, for example, albumins; organic solvents such as, for example, formamide; quaternary ammonium salts; polyanions such as, for example, dextran sulfate; binding enhancers, for example, polyalkylene glycols; polysaccharides such as, for example, dextran or trehalose. The medium may also comprise agents for preventing the formation of blood clots. Such agents are well known in the art and include, but are not limited to, EDTA, EGTA, citrate, heparin, for example. The medium may also comprise one or more preservatives such as, but not limited to, sodium azide, neomycin sulfate, PROCLIN® 300, Streptomycin, for example. The medium may additionally comprise one or more surfactants. Any of the above materials, if employed, is present in a concentration or amount sufficient to achieve the desired effect or function.

One or more incubation periods may be applied to the medium at one or more intervals including any intervals between additions of various reagents employed in an assay including those mentioned above. The medium is usually incubated at a temperature and for a time sufficient for binding of various components of the reagents and binding of vitamin D in the sample to occur. Moderate temperatures are normally employed for carrying out the method and usually constant temperature, preferably, room temperature, during the period of the measurement. In some examples, incubation temperatures range from about 5° to about 99° C., or from about 15° C. to about 70° C., or from about 20° C. to about 45° C., for example. The time period for the incubation, in some examples, is about 0.2 seconds to about 24 hours, or about 1 second to about 6 hours, or about 2 seconds to about 1 hour, or about 1 minute to about 15 minutes, for example. The time period depends on the temperature of the medium and the rate of binding of the various reagents, which is determined by the association rate constant, the concentration, the binding constant and dissociation rate constant.

In an example of a method for determining a vitamin D analyte in a sample suspected of containing the vitamin D analyte, a combination is provided in a medium where the combination includes the sample, a releasing agent (if the sample has not been pretreated to release the vitamin D analyte from endogenous binding substances), an antibody for vitamin D, and a labeled vitamin D analog where the label is a poly(amino acid) label or a non-poly(amino acid) label. The medium is examined for one or both of the presence and amount of one or both of a complex comprising vitamin D and the antibody for vitamin D or a complex comprising the labeled compound and antibody for vitamin D. The presence and/or the amount of one or both of the complexes indicates the presence and/or amount of the vitamin D analyte in the sample.

Some known assays utilize a signal producing system (sps) that employs first and second sps members. The designation "first" and "second" is completely arbitrary and is not meant to suggest any order or ranking among the sps members or any order of addition of the sps members in the present methods. The sps members may be related in that activation of one member of the sps produces a product such as, e.g., light or an activated product, which results in activation of another member of the sps.

In some embodiments of assays, the sps members comprise a sensitizer such as, for example, a photosensitizer, and a chemiluminescent composition where activation of the sensitizer results in a product that activates the chemiluminescent composition. The second sps member usually generates a detectable signal that relates to the amount of bound and/or unbound sps member, i.e., the amount of sps member bound or not bound to the vitamin D analyte being detected or to a compound in accordance with the principles described herein. In some examples in accordance with the principles described herein, one of either the sensitizer reagent or the chemiluminescent reagent comprises the present compound reagent.

In a particular example, an induced luminescence immunoassay may be employed. The induced luminescence immunoassay is referred to in U.S. Pat. No. 5,340,716 (Ullman), which disclosure is incorporated herein by reference. In one approach, the assay uses a particle having associated therewith a photosensitizer where a vitamin D analog is bound to the particle (particle-compound reagent). The chemiluminescent reagent comprises an antibody for the vitamin D analyte. The vitamin D analyte competes with the particle-compound reagent for binding to the antibody for vitamin D. If the vitamin D analyte is present, the fewer is the number of molecules of particle-compound reagent that come into close proximity with the chemiluminescent reagent. Therefore, there will be a decrease in the assay signal. The photosensitizer generates singlet oxygen and activates the chemiluminescent reagent when the two labels are in close proximity. The activated chemiluminescent reagent subsequently produces light. The amount of light produced is related to the amount of the complex formed, which in turn is related to the amount of vitamin D analyte present in the sample.

In another particular example of an induced luminescence immunoassay, the assay uses a particle having associated therewith a chemiluminescent compound where a vitamin D analog is bound to the particle (particle-compound reagent). The photosensitizer reagent comprises an antibody for vitamin D. The vitamin D analyte competes with the particle-compound reagent for binding to the antibody for vitamin D. If the vitamin D analyte is present, the fewer is the number of molecules of particle-compound reagent that come into close proximity with the photosensitizer reagent. Therefore, there will be a decrease in the assay signal. The photosensitizer generates singlet oxygen and activates the chemiluminescent compound of the particle-compound reagent when the two labels are in close proximity. The activated chemiluminescent compound subsequently produces light. The amount of light produced is related to the amount of the complex formed, which in turn is related to the amount of vitamin D analyte present in the sample.

In another particular example of an induced luminescence assay, a photosensitizer particle is employed that is conjugated to a binding partner for a small molecule such as, for example, avidin or streptavidin (which are binding partners for biotin). A vitamin D analog that comprises biotin (compound-biotin reagent) is also employed. A chemiluminescent reagent that comprises an antibody for the vitamin D analyte is employed as part of the detection system. The reaction medium is incubated to allow the avidin or streptavidin of the photosensitizer particles to bind to the compound-biotin reagent by virtue of the binding between avidin and biotin and to also allow the antibody for the vitamin D analyte that is part of the chemiluminescent reagent to bind to the vitamin D analyte or to vitamin D analog that is now attached to the photosensitizer particles. Then, the medium is irradiated with light to excite the photosensitizer, which is capable in its excited state of activating oxygen to a singlet state. Because less of the chemiluminescent reagent is now in close proximity to the photosensitizer because of the presence of the vitamin D analyte, there is less activation of the chemiluminescent reagent by the singlet oxygen and less luminescence. The medium is then examined for the presence and/or the amount of luminescence or light emitted, the presence thereof being related to the presence and/or amount of the vitamin D analyte where a decrease in signal is observed in the presence of the vitamin D analyte.

In another particular example of an induced luminescence assay, a photosensitizer particle is employed that is conjugated to a binding partner for a small molecule such as, for example, avidin or streptavidin (which are binding partners for biotin). A conjugate reagent comprises an antibody for the vitamin D analyte conjugated to biotin. A vitamin D analog is employed where the compound is attached to a chemiluminescent particle (chemiluminescent-compound reagent) is also employed. The reaction medium is incubated to allow the avidin or streptavidin of the photosensitizer particles to bind to the antibody-biotin reagent by virtue of the binding between avidin and biotin and to also allow antibody for the vitamin D analyte to bind to the vitamin D analyte if present in the sample and to the vitamin D analog that is part of the chemiluminescent-compound reagent. Then, the medium is irradiated with light to excite the photosensitizer, which is capable in its excited state of activating oxygen to a singlet state. Because less of the chemiluminescent-compound reagent is now in close proximity to the photosensitizer because of the presence of the vitamin D analyte, there is less activation of the chemiluminescent reagent by the singlet oxygen and less luminescence. The medium is then examined for the presence and/or the amount of luminescence or light emitted, the presence thereof being related to the presence and/or amount of the vitamin D analyte where a decrease in signal is observed in the presence of the vitamin D analyte.

Another example, by way of illustration and not limitation, of an assay format for detection of a vitamin D analyte is the ACMIA assay format. For the ACMIA assay format, chrome particles, which are coated with a vitamin D analog (chrome particle reagent), are employed as a first component. A second component is an antibody for the vitamin D analyte. This antibody, crosslinked to a reporter enzyme (for example, β-galactosidase) to form an antibody-enzyme conjugate, is added to a reaction vessel in an excess amount, i.e., an amount greater than that required to bind all of the vitamin D analyte that might be present in a sample. A sample, which is previously subjected to treatment with a releasing agent, is treated with an antibody for the vitamin D analyte, which binds to the vitamin D analyte in the sample. The antibody-enzyme conjugate is mixed with sample in the medium to allow the vitamin D analyte to bind to the antibody. Next, the chrome particle reagent is added to bind up any excess antibody-enzyme conjugate. Then, a magnet is applied, which pulls all of the chrome particles and excess antibody-enzyme out of the suspension, and the supernatant is transferred to a final reaction container. The substrate of the reporter enzyme is added to the final reaction container, and the enzyme activity is measured spectrophotometrically as a change in absorbance over time. The amount of this signal is related to the amount of the vitamin D analyte in the sample.

Another example of an assay for vitamin D in accordance with the principles described herein is an acridinium ester label immunoassay using paramagnetic particles as a solid phase (ADVIA immunoassay). The detection system employed for this example of a vitamin D assay includes a small molecule-labeled vitamin D analog (capture moiety) as the small molecule conjugate or capture conjugate, binding partner for the small molecule-coated paramagnetic latex particles as a solid phase (SP), and an acridinium ester labeled antibody for the vitamin D analyte (detection antibody). The small molecule may be, for example, biotin or fluorescein and the respective binding partner may be streptavidin or antibody for fluorescein. The vitamin D analog may be linked to the small molecule directly or through a linking group such as, for example, a protein, e.g., bovine serum albumin (BSA). Vitamin D analyte in a patient sample competes with vitamin D analog of the capture moiety for binding to the acridinium ester labeled detection anti-vitamin D antibody. The sample suspected of containing vitamin D is subjected to a pretreatment with 1,8-ANS. The assay may be carried out on a Centaur®, Centaur® XP or Centaur® CP apparatus (Siemens Healthcare Diagnostics Inc., Newark Del.) in accordance with the manufacturer's directions supplied therewith.

Another example of an assay for a vitamin D analyte in accordance with the principles described herein is an acridinium ester label immunoassay using paramagnetic particles as a solid phase (ADVIA immunoassay). The detection system employed for this example of a vitamin D assay includes a small molecule-labeled antibody for the vitamin D analyte (capture antibody) as the biotin conjugate or capture conjugate, streptavidin-coated paramagnetic latex particles as a solid phase (SP), and an acridinium ester labeled vitamin D analog (detection hapten). The acridinium ester label may be directly bound to the vitamin D analog to form the detection hapten or a linking group may be employed including, for example, a protein such as, e.g., BSA. Vitamin D analyte in a patient sample competes with the acridinium ester labeled detection hapten for binding with anti-vitamin D antibody. The sample suspected of containing vitamin D is subjected to a pretreatment with 1,8-ANS. The assay may be carried out on a Centaur®, Centaur® XP or Centaur® CP apparatus (Siemens Healthcare Diagnostics Inc., Newark Del.) in accordance with the manufacturer's directions supplied therewith. In variations of the above acridinium ester assays, the small molecule may be, for example, biotin or fluorescein.

The concentration of the vitamin D analyte in a sample that may be assayed generally varies from about $10^{-5}$ to about $10^{-17}$ M, or from about $10^{-6}$ to about $10^{-14}$ M, for example. Considerations such as whether the assay is qualitative, semi-quantitative or quantitative (relative to the amount of the vitamin D analyte present in the sample), the particular detection technique and the expected concentration of the vitamin D analyte normally determine the concentrations of the various reagents.

The concentrations of the various reagents in the assay medium will generally be determined by the concentration range of interest of the vitamin D analyte, the nature of the assay, and the like. However, the final concentration of each of the reagents is normally determined empirically to optimize the sensitivity of the assay over the range of interest. That is, a variation in concentration of vitamin D analyte that is of significance should provide an accurately measurable signal difference. Considerations such as the nature of the signal producing system and the nature of the analytes normally determine the concentrations of the various reagents.

Examples of Assays for Epimers of Vitamin D Employing Reagents in Accordance with the Principles Described Herein As mentioned above, one particular example in accordance with the principles described herein is directed to methods of determining one or both of the presence and the amount of epimers of vitamin D in a sample suspected of containing epimers of vitamin D. Any of the above assay formats may be employed using an antibody raised against an immunogen that is a compound of the Formula I wherein Z is an immunogenic carrier. In some examples the immunogen is a compound of the Formula IIa (see FIG. 3). In some examples the immunogen is a compound of the Formula IIb (see FIG. 5). In some examples, the antibody employed is antibody 4G8.2 or antibody 8F10.2 Antibodies produced from other immunogens consistent with the principles described herein may be employed in any of the above assay formats.

One example of an assay for an epimer of vitamin D is an induced luminescence assay for the detection of 3-epi-25-hydroxyvitamin $D_3$ in a sample suspected of containing 3-epi-25-hydroxyvitamin $D_3$. The sample is treated with a releasing agent to release 3-epi-25-hydroxyvitamin $D_3$ from endogenous binding moieties. Then, the sample is combined with a reagent that comprises antibody 4G8.2, which is an antibody for 3-epi-25-hydroxyvitamin $D_3$, conjugated to biotin (antibody-biotin reagent) in a reaction medium, which is incubated to allow the binding between the antibody-biotin reagent and the 3-epi-25-hydroxyvitamin $D_3$ analyte. Then, a chemiluminescent reagent is added where the reagent comprises a compound of the Formula IIa as a vitamin D analog attached to a chemiluminescent particle. The chemiluminescent reagent binds to excess antibody-biotin reagent, that is, antibody-biotin reagent that does not bind to 3-epi-25-hydroxyvitamin $D_3$ analyte in the sample. Then, a photosensitizer particle reagent is added that is conjugated to a streptavidin. The reaction medium is incubated to allow the streptavidin of the photosensitizer particles to bind to the antibody-biotin reagent by virtue of the binding between streptavidin and biotin. Then, the medium is irradiated with light to excite the photosensitizer, which is capable in its excited state of activating oxygen to a singlet state. Because less of the chemiluminescent reagent is now in close proximity to the photosensitizer because of the presence of the 3-epi-25-hydroxyvitamin $D_3$ analyte, there is less activation of the chemiluminescent reagent by the singlet oxygen and less luminescence. The medium is then examined for the presence and/or the amount of luminescence or light emitted, the presence thereof being related to the presence and/or amount of the 3-epi-25-hydroxyvitamin $D_3$ analyte where a decrease in signal is observed in the presence of the 3-epi-25-hydroxyvitamin $D_3$ analyte.

Examples of Assays for Vitamin D Analytes Employing Antibodies in Accordance with the Principles Described Herein as Blocking Antibodies Antibodies in accordance with the principles described herein may be employed to minimize or eliminate 3-epimer cross-reactivity in assays for non-epimeric forms of vitamin D analytes. Over-estimation of total non-epimeric vitamin D analyte caused by the cross-reactivity of 3-epimer vitamin D with an antibody for vitamin D analyte can be substantially avoided employing, as blocking agents, antibodies prepared against immunogens that are a compound of the Formula I wherein Z is an immunogenic carrier.

In one example of an assay for non-epimeric vitamin D analyte, the assay uses, as a chemiluminescent reagent, a chemibead reagent that comprises an olefinic dye and 25-hydroxyvitamin $D_3$ as a vitamin D analog. A sample suspected of containing non-epimeric vitamin D analyte is combined in an assay medium with a biotinylated antibody for the non-epimeric vitamin D analyte and a second antibody that is antibody 8F10 and then with the chemibead reagent. The chemibeads bind to the fraction of the monoclonal antibody binding sites that is not occupied by non-epimeric vitamin D analyte from the sample. Antibody 8F10 binds to 3-epi-25-hydroxyvitamin $D_3$ that is present in the sample and that interferes in the determination by cross-reaction with the biotinylated antibody. Subsequently, streptavidin coupled sensitizer beads comprising a photosensitizer (sensibeads) are added to the reaction mixture. This leads to the formation of chemibead/sensibead pairs whose concentration is inversely related to a concentration of non-epimeric vitamin D analyte in the sample. Upon illumination at 680 nm, the sensitizer beads generate singlet oxygen which diffuses into the chemibeads, which are paired with sensibeads, reacts with the olefinic dye in the chemiluminescent and triggers a chemiluminescent signal at approximately 612 nm which is inversely related to the non-epimeric vitamin D analyte concentration.

Examples of Assays for Vitamin D Analytes Employing a Labeled Compound in Accordance with the Principles Described Herein Assays for vitamin D analytes may be carried out using a compound of the Formula I wherein Z is a poly(amino acid) label, or a non-poly(amino acid) label or a support.

In an example, by way of illustration and not limitation, of an assay for detection of vitamin D analyte, an ACMIA assay format is employed. Chrome particles, which are coated with a vitamin D analog that is a compound of the Formula I wherein Z is a non-poly(amino acid) label that is the chrome particle (chrome particle reagent), are employed as a first component. A second component is an antibody for vitamin D analyte. This antibody, crosslinked to a reporter enzyme (for example, β-galactosidase) to form an antibody-enzyme conjugate, is added to a reaction vessel in an excess amount, i.e., an amount greater than that required to bind all of the vitamin D analyte that might be present in a sample. A sample, which is previously subjected to treatment with a releasing agent, is treated with an antibody for vitamin D, which binds to vitamin D analyte in the sample. The antibody-enzyme conjugate is mixed with sample in the medium to allow the vitamin D analyte to bind to the antibody. Next, the chrome particle reagent is added to bind up any excess antibody-enzyme conjugate. Then, a magnet is applied, which pulls all of the chrome particles and excess antibody-enzyme out of the suspension, and the supernatant is transferred to a final reaction container. The substrate of the reporter enzyme is added to the final reaction container, and the enzyme activity is measured spectrophotometrically as a change in absorbance over time. The amount of this signal is related to the amount of vitamin D analyte in the sample.

In the above example, an antibody in accordance with the principles described herein may be employed to block binding of 3-epi-25-hydroxyvitamin $D_3$, which may be present in the sample, to the antibody for the vitamin D analyte. The anti-3-epi-25-hydroxyvitamin $D_3$ antibody may be, an antibody raised against an immunogen that is a compound of Formula I wherein Z is an immunogenic carrier.

Examination Step

In a next step of an assay method, the medium is examined for the presence of a complex comprising the vitamin D analyte and antibody for the vitamin D analyte and/or a complex comprising a vitamin D analog and antibody for vitamin D. The presence and/or amount of one or both of the complexes indicates the presence and/or amount of the vitamin D analyte in the sample.

The phrase "measuring the amount of a vitamin D analyte" refers to the quantitative, semiquantitative and qualitative determination of vitamin D Methods that are quantitative, semiquantitative and qualitative, as well as all other methods for determining the vitamin D analyte, are considered to be methods of measuring the amount of the vitamin D analyte. For example, a method, which merely detects the presence or absence of the vitamin D analyte in a sample suspected of containing the vitamin D analyte, is considered to be included within the scope of the present invention. The terms "detecting" and "determining," as well as other common synonyms for measuring, are contemplated within the scope of the present invention.

In many embodiments the examination of the medium involves detection of a signal from the medium. The presence and/or amount of the signal is related to the presence and/or amount of the vitamin D analyte in the sample. The particular mode of detection depends on the nature of the signal producing system. As discussed above, there are numerous methods by which a label of a signal producing signal can produce a signal detectable by external means. Activation of a signal producing system depends on the nature of the signal producing system members.

Temperatures during measurements generally range from about 10° C. to about 70° C. or from about 20° C. to about 45° C., or about 20° C. to about 25° C., for example. In one approach standard curves are formed using known concentrations of vitamin D analyte. Calibrators and other controls may also be used.

Luminescence or light produced from any label can be measured visually, photographically, actinometrically, spectrophotometrically, such as by using a photomultiplier or a photodiode, or by any other convenient means to determine the amount thereof, which is related to the amount of vitamin D analyte in the medium. The examination for presence and/or amount of the signal also includes the detection of the signal, which is generally merely a step in which the signal is read. The signal is normally read using an instrument, the nature of which depends on the nature of the signal. The instrument may be, but is not limited to, a spectrophotometer, fluorometer, absorption spectrometer, luminometer, and chemiluminometer, for example.

Kits Comprising Reagents for Conducting Assays

Kits comprising reagents for conducting assays can be formulated based on the nature of a particular assay. In some examples in accordance with the principles described herein a kit can comprise a binding partner such as, for example, an antibody raised against an immunogen that is a compound of the Formula I wherein Z is an immunogenic carrier. In some examples in accordance with the principles described herein, a kit can comprise a reagent that is a compound of the Formula I wherein Z is a poly(amino acid) label moiety or a non-poly(amino acid) label moiety including a support. A kit may also include other reagents for conducting a particular assay for a vitamin D analyte. In some embodiments a kit comprises in packaged combination a biotin-binding partner such as, for example, avidin or streptavidin, associated with a particle, biotinylated compound of Formula I and a labeled antibody for the vitamin D analyte. The kit may further include other reagents for performing the assay, the nature of which depend upon the particular assay format.

The reagents may each be in separate containers or various reagents can be combined in one or more containers depending on the cross-reactivity and stability of the reagents. The kit can further include other separately packaged reagents for conducting an assay such as additional specific binding pair members, signal producing system members, and ancillary reagents, for example.

The relative amounts of the various reagents in the kits can be varied widely to provide for concentrations of the reagents that substantially optimize the reactions that need to occur during the present methods and further to optimize substantially the sensitivity of an assay. Under appropriate circumstances one or more of the reagents in the kit can be provided as a dry powder, usually lyophilized, including excipients, which on dissolution will provide for a reagent solution having the appropriate concentrations for performing a method or assay using a compound reagent in accordance with the principles described herein. The kit can further include a written description of a method utilizing reagents that include a compound reagent in accordance with the principles described herein.

Pharmaceutical Compositions Containing Compounds in Accordance with the Principles Described Herein Examples of compounds and antibodies in accordance with the principles described herein can have therapeutic activity. These compounds may be administered in therapeutically effective amount, which is an amount to provide treatment of a particular disease state associated with vitamin D. Administration of the examples of compounds in accordance with the principles described herein can be by means of any of the accepted modes of administration for agents that serve similar utilities. The compounds can be used both prophylactically and therapeutically.

The amount of compound administered is dependent on one or more of the subject and disease state being treated, the severity of the affliction, the manner and schedule of administration (e.g., oral administration) and the judgment of the prescribing physician.

In employing the compounds of this invention for treatment of the above conditions, any pharmaceutically acceptable mode of administration can be used. The compounds in accordance with the principles described herein can be administered either alone or in combination with other pharmaceutically acceptable excipients, including, but not limited to, solid, semi-solid, liquid or aerosol dosage forms, such as, for example, tablets, capsules, powders, liquids, injectables, suspensions, suppositories, and aerosols, for example. The compounds can also be administered in sustained or controlled release dosage forms, including depot injections, osmotic pumps, pills, and transdermal (including electrotransport) patches, for example, for the prolonged administration of the compound at a predetermined rate, preferably in unit dosage forms suitable for single administration of precise dosages. The pharmaceutical compositions include one or more conventional pharmaceutical carriers or excipients and a compound in accordance with the principles described herein. In addition, these compositions may include other medicinal agents, pharmaceutical agents, carriers, and adjuvants, for example.

Depending on the intended mode of administration, a pharmaceutically acceptable composition will contain about 0.1% to about 90%, by weight of a compound in accordance with the principles described herein, the remainder being suitable pharmaceutical excipients and carriers, for example.

One mode of administration for the conditions detailed above is oral, using a convenient daily dosage regimen, which can be adjusted according to the degree of affliction. For such oral administration, a pharmaceutically acceptable composition is formed by the incorporation of any of the normally employed excipients, such as, for example, mannitol, lactose, starch, povidone, magnesium stearate, sodium saccharine, talcum, cellulose, croscarmellose sodium, glucose, gelatin, sucrose, and magnesium carbonate, for example, and combinations of two or more thereof. Such compositions may be solutions, suspensions, tablets, dispersible tablets, pills, capsules, powders, or sustained release formulations, for example.

In one approach by way of illustration and not limitation, a composition may be in the form of a pill or tablet and may contain, along with a compound in accordance with the principles described herein, a diluent such as lactose, sucrose, or dicalcium phosphate, for example, or combination of two or more thereof; a lubricant such as magnesium stearate, for example; a disintegrant such as croscarmellose sodium, for example; and a binder such as starch, gum acacia, polyvinylpyrrolidine, gelatin, cellulose and derivatives thereof, for example.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients include, but are not limited to, water, saline, dextrose, glycerol and ethanol, for example. In addition, the pharmaceutical compositions to be administered may also contain minor amounts of non-toxic auxiliary substances such as wetting or emulsifying agents, pH buffering agents, and solubility enhancers, for example, such as, for example, sodium acetate, polyoxyethylene, sorbitan monolaurate, triethanolamine oleate, and cyclodextrins.

In one example in accordance with the principles described herein, a pharmaceutical composition comprises a compound of the formula:

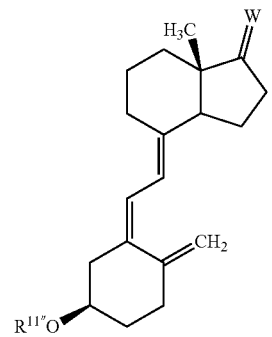

wherein W is O or N—O—(CH$_2$)$_{n''}$C(O)—Z'', n'' is an integer from 1 to 10,

R$^{11''}$ is H, alkyl, or acyl, and

Z'' is OR$^8$ wherein R$^8$ is H, alkyl, or NR$^9$R$^{10}$ wherein R$^9$ and R$^{10}$ are independently H or alkyl.

The phrase "at least" as used herein means that the number of specified items may be equal to or greater than the number recited. The phrase "about" as used herein means that the number recited may differ by plus or minus 10%; for example, "about 5" means a range of 4.5 to 5.5.

The following discussion is directed to specific examples in accordance with the principles described herein by way of illustration and not limitation; the specific examples are not intended to limit the scope of the present disclosure and the appended claims. Numerous modifications and alternative compositions, methods, and systems may be devised without departing from the spirit and scope of the present disclosure.

EXAMPLES

Unless otherwise indicated, materials in the experiments below may be purchased from the Sigma-Aldrich Chemical Corporation (St. Louis Mo.) or Fluka Chemical Corporation (Milwaukee Wis.). Parts and percentages disclosed herein are by weight to volume unless otherwise indicated.

Definitions
mg=milligram
g=gram(s)
ng=nanogram(s)
mL=milliliter(s)
μL=microliter(s)
μmol=micromolar
° C.=degrees Centigrade
min=minute(s)
sec=second(s)
hr=hour(s)
w/v=weight to volume
TLC=thin layer chromatography
HPLC=high performance liquid chromatography
EDA=ethylenediamine
EtOAc=ethyl acetate
DMF=dimethylformamide
DMSO=dimethylsulfoxide
MeOP=1-methoxy-2-propanol
MES=2-(N-morpholino)ethanesulfonic acid
CMO=carboxymethoxyoxime
TMB=tetramethyl benzidine
SNHS=sulfo-N-hydroxysuccinimide
High pH Wash Buffer=5.5 mM $Na_3PO_4$+4.4 mM $Na_2CO_3$, pH 11
Hapten Wash Buffer=50 mM HEPES, 300 mM NaCl, 1 mM EDTA, 0.1% TRITON® X405, 0.15% PROCLIN® preservative, and 1 mg/ml neomycin
DI=deionized
ELISA=enzyme-linked immunosorbent assay
UPA=Ultra Particle Analyzer
LOCI=luminescent oxygen channeling immunoassay
BSA=bovine serum albumin
BGG=bovine gamma globulin
mIgG=mouse immunoglobulin
MS=mass spectrometry

Example 1

Preparation of Compounds of FIG. 2 where $R^{11}$ is Acetyl

5-Androsten-3α-ol-17-one acetate (VIII) (100 mg) was reacted with ethylene glycol (0.245 ml) and p-toluenesulfonic acid monohydrate (4 mg) in benzene under reflux overnight to give 5-androsten-3α-ol-17-one acetate ethylene ketal (IX) (112 mg). The ethylene ketal IX (112 mg) was brominated with N-bromosuccinimide (69 mg)/azoisobutyronitrile (3.3 mg) in hexane (13 ml) under reflux for 30 minutes to give compound X, followed by dehydrobromination with tetrabutylammonium fluoride (1M in THF, 1.6 ml) in THF (7.3 ml) at room temperature for 2 hours to give androsta-5,7-dien-3α-ol-17-one acetate ethylene ketal (XI) (55 mg). Androsta-5,7-dien-3α-ol-17-one acetate ethylene ketal (XI) (55 mg) was reacted with 1N sodium hydroxide (2 mL) in methanol (10 ml) at room temperature for about 5 hours to give androsta-5,7-dien-3α-ol-17-one ethylene ketal (XII) (48 mg). Androsta-5,7-dien-3α-ol-17-one ethylene ketal (XII) (48 mg) was reacted with p-toluenesulfonic acid monohydrate (35 mg) in a mixture of acetone (5 mL) and water (0.2 mL) at room temperature overnight to give androsta-5,7-dien-3α-ol-17-one (XIII) (43.4 mg). Androsta-5,7-dien-3α-ol-17-one (XIII) (43.4 mg) was irradiated under 450 w mercury lamp with a VYCOR® filter (Ace Glass Incorporated, Vineland, N.J.) in ether (1100 ml) at −20 to 0° C. for 5 minutes to give pre-HMCHEMOIO, which was refluxed in ethanol (15 ml) for 3 hours to produce HMCHEMOIO (VII) (13.5 mg).

The HMCHEMOIO (VII) (13.5 mg) from above was reacted with O-(carboxymethyl)hydroxylamine hemihydrochloride (12 mg) and sodium acetate (24 mg) in 1 ml methanol for overnight at room temperature to give HMCHEMOIO-CMO (13.2 mg) (compound of the Formula XX in FIG. 3 where n=1).

Cationized BSA was prepared as follows: Triethylenetetraamine (0.5 mL) (compound of the Formula XXI in FIG. 3 where each r=1 and s=1) was added to 4.5 ml 50 mM MES buffer pH6, and the pH was adjusted to 6 followed by addition of 20 mg BSA. The combination was mixed to completely dissolve the components. EDAC (5 mg) was added to the above solution each hour for 5 hours. The solution was washed in a 10 mL AMICON® cell (Amicon Inc., Beverly Mass.) with 10×10 mL washing buffer (10 mM phosphate+300 nM NaCl) at pH7. Then, 100 mg TWEEN®20 was added to a 50-mL round bottom flask. Washing buffer (50 mL) was added and the mixture was stirred for 10 min to disperse Tween 20. The cationized BSA (compound of the Formula XXIa in FIG. 3 where each r=1 and s=2) was stored in washing buffer with 0.2% TWEEN® 20 at about 5 mg/mL.

For preparation of HMCHEMOIO-CMO BSA (compound of the Formula IIa in FIG. 3), EDAC (25 mg) and 10 mg NHS were placed into a 10 ml flask with 13.2 mg HMCHEMOIO-CMO (XX) prepared as described above. DMF (0.5 ml) was added to the flask. The mixture was stirred for 24 hours at room temperature to give activated HMCHEMOIO-CMO. The solution was clear. TLC (1:1 Ethyl Acetate:Methanol) indicated no remaining starting material.

The activated HMCHEMOIO-CMO from above was added drop wise to the cationized BSA solution from above, and the mixture was stirred overnight at room temperature. The mixture was transferred to an Amicon® cell (Amicon Inc., Beverly Mass.), and then washed with 5×10 ml washing buffer and concentrated (30,000 cut off) to around 4 mL. The mixture was further separated on an SD-25 column (GE Healthcare Bio-Sciences, Pittsburgh Pa.) using washing buffer pH 7.0 as an elutant to give a mixture of HMCHEMOIO-CMO BSA compounds (mixture as discussed above with regard to compounds of the Formula IIa in FIG. 3).

Example 2

Preparation of Antibodies

AJ strain of mice (females, at least eight weeks old) was immunized to generate monoclonal antibodies. The first immunization was 100 μg of immunogen (HMCHEMOIO-CMO BSA) from above in a volume of 100 μl with Complete Fruends' adjuvant (from Sigma-Aldrich, Cat # F5881). Three weeks later, a boost immunization with the same immunogen was given with 100 μg in a volume of 100 μL with Incomplete Fruend's adjuvant (from Sigma-Aldrich Cat # F5506). Subsequently, after another 3 weeks, a second booster immunization with the same immunogen was given with 100 μg in a volume of 100 μL with Incomplete Fruends' Adjuvant. One week following last booster immunization, mice were bled and anti-sera were tested in ELISA for anti-3-epimer antibodies. Subsequently, a prefusion boost was given on three consecutive days before fusion with the same immunogen (20 μg in a volume of 50 μL in PBS without any adjuvant. On the fourth day, mice were sacrificed and splenectomy was performed. Spleen cells were removed and fusion was performed by standard methods using a non-secreting murine myeloma cell line designated P3-X63Ag8.653 (ATCC CRL-1580™). Cloning was done by standard methods.

The clones were screened by binding and inhibition ELISA. The following binding ELISA immunoassay procedure according to the following protocol. Plates were coated with 3-epimer-conjugated to ovalbumin prepared in a manner similar to that described above for the BSA conjugate at 1 μg/mL in PBS at 50 μL per well. Plate coating was performed for 1 hour or more at room temperature. The plates were then flicked dry and blocked with 200 μL per well of blocking buffer diluent (0.5% Casein solution in PBS containing 0.05% Tween® 20). Plate blocking was performed for 1 hour or overnight at 2° C.-8° C. The plates were then washed three times and flicked dry. The monoclonal antibody to be screened was then added to each well as follows: 25 μL of PBS mixed with 25 μL of culture supernatant transferred from the corresponding well in the fusion growth plate. Incubation was for about 1 hour at room temperature with plate shaking. The plate was washed using a plate washer (BioTek, Winooski Vt.) with plate stacker with the washing buffer being MILLI-Q® water (Millipore Corporation, Billerica, Mass.) containing 0.05% Tween® 20. An enzyme conjugate (goat anti-mouse IgG coupled to HRP diluted in blocking buffer diluent to 1:3000 was added at 50 μL per well. Incubation was performed for about 1 hour at room temperature with shaking. The plate was then washed and a chromogenic solution (TMB from Moss Substrates, Pasadena Md.) was added at a volume of 100 μL per well for ten minutes at room temperature. Plates were read at 650 nm using an ELISA plate reader.

Based on the above screening technique, hybridomas producing suitable monoclonal antibodies were selected. One such monoclonal antibody was designated antibody 8F10 and is an IgG2a kappa antibody. Another such monoclonal antibody was designated antibody 4G8 and is an IgG2a kappa antibody.

Additionally, clones were also screened using an inhibition ELISA procedure according to the following protocol. Plates were coated with 3-epimer-conjugated to ovalbumin at 1 μg/mL in phosphate buffered saline at 50 μL per well. Plate coating was performed for 1 hour or more at room temperature or overnight at about 2° C. to 8° C. The plates were then flicked dry and blocked with 200 μL per well of blocking buffer diluent (0.5% Casein solution in PBS containing 0.05% TWEEN® 20). Plate blocking was performed by incubation for 30 min or more at room temperature with plate shaking. The plates were washed. The monoclonal antibody to be screened was then added to each well along with free 3-epimer as follows: 25 μL per well culture supernatant transferred from the corresponding well in the fusion growth plate and added 25 μL of 2 μg/mL of 3-epimer-25OH Vitamin $D_3$. Incubation was for about 1 hour at room temperature with plate shaking. The plate was washed using a plate washer (BioTek, Winooski Vt.) with plate stacker with the washing buffer being MILLI-Q® water (Millipore Corporation, Billerica, Mass.) containing 0.05% TWEEN® 20. An enzyme conjugate (goat anti-mouse IgG coupled to HRP diluted in blocking buffer diluent to 1:3000 was added at 50 μL per well. Incubation was performed for about 1 hour at room temperature with shaking. The plate was then washed and a chromogenic solution (TMB from Moss Substrates, Pasadena Md.) was added at a volume of 100 μL per well. If a desired antibody was present in the hybridoma supernatant, then a decrease in optical density was observed compared to the well containing no free 3-epimer. 25OH Vitamin $D_3$ was used in place of free 3-epimer-25 OH Vitamin $D_3$ as a control to monitor the specificity of the antibodies. Antibodies binding to 3-epimer and not binding to 25OH vitamin D3 were selected.

Polyclonal antibody generation: Rabbits were immunized with 500 μg/dose of HMCHEMOIO-CMO BSA. One primary and five booster immunizations two weeks apart were performed and two test bleeds and one production bleed were collected and anti-sera was tested in ELISA as described above.

Example 3

Immunoassay for 25OH Vitamin D

Immunoassay Procedure

The 25OH Vitamin D (25(OH)D) immunoassay format employed was a homogeneous competitive chemiluminescent immunoassay based on LOCK) assay technology. The assay was performed on the Siemens Dimension® EXL automated integrated clinical chemistry system (Siemens Healthcare Diagnostics Inc., Deerfield, Ill.). The assay measured the total concentration of $25(OH)D_2$ and/or $25(OH)D_3$ in serum and plasma samples. The LOCI® assay reagents included a releasing reagent, two synthetic bead reagents and a biotinylated monoclonal anti-25OH vitamin D antibody reagent. The first bead reagent (designated "Sensibeads") was coated with streptavidin and contained a photosensitive dye. The second bead reagent (designated "Chemibeads") was coated with a $25(OH)D_3$ analog and contained chemiluminescent dye. Sample was incubated with the releasing reagent to release 25(OH)D molecules including 3-epimeric compounds from vitamin D binding proteins. The reaction mixture was then incubated with biotinylated antibody to form a 25(OH)D-biotinylated antibody complex. Because the biotinylated antibody (a sheep monoclonal antibody) cross reacted with 3-epi-25(OH)D, 100 μg/mL of anti-3-epimer-VD antibody 8F10.1 was added to minimize assay signal coming from the 3-epimer vitamin D compounds. Chemibeads were added to bind excess free biotinylated antibody. Sensibeads were then added to bind to the biotin portion of the biotinylated antibody. Aggregates of Chemibead-analog/antibody-biotin/streptavidin-Sensibeads were formed as a result. Illumination of the reaction mixture with light at 680 nm generates singlet oxygen from Sensibeads, which diffused into the Chemibeads and triggered a chemiluminescent reaction. The resulting chemiluminescent signal was measured at 612 nm and is inversely proportional to the concentration of total 25(OH)D in the sample.

Preparation of Reagents for Immunoassay

Synthesis of 25(OH)D$_3$ Chemibeads—The 25(OH)D$_3$ Chemibeads were synthesized by coupling EPRM-EDA with 25(OH)D$_3$ carbamate. The materials employed were EPRM-EDA Beads, 1-Ethyl-3-(3-Dimethyl Aminopropyl) Carbodiimide (EDAC) Fluka Sulfo-N-Hydroxysuccinimide (SNHS), 25(OH)D$_3$-3-Carbamate, GAFAC® surfactant solution 16%, Anhydrous DMSO, 50 mM MES pH6 Buffer containing 10% MeOP and 1% GAFAC® surfactant.

Preparation of EPRM-EDA beads—EPRM beads (2000 mg, 20.0 mL) are added to a 40-mL vial. The EPRM beads are prepared by a procedure similar to that described in U.S. Pat. No. 7,179,660 and the chemiluminescent compound is 2-(4-(N,N, di-tetradecyl)-anilino-3-phenyl thioxene with europium chelate. EDA (800 mg, 890 µL) is combined with 10 mL MES pH 6 buffer (the "Buffer") and about 4.2 mL 6N HCl. The pH of the mixture is, or is adjusted to be, about 6.9. The EDA solution is added to the EPRM beads with vortexing and the mixture is rocked at room temperature for 15 minutes. Sodium cyanoborohydride (400 mg) is combined in a 15 mL vial with 10 mL DI water and the combination is added to the bead mixture from above. The mixture is shaken at 37° C. for 18-20 hours. The beads are transferred to six 40 mL centrifuge tubes. MES buffer is added to bring the volume to 35 mL and the mixture is centrifuged at 19,000 rpm for 30 min. The supernatant is decanted and the beads are re-suspended in 2 mL of the Buffer with a stir-rod and additional Buffer is added to 35 mL. The mixture is sonicated at 18 Watts power for 30 sec, using ice to keep the mixture cold. The wash/sonication step is performed 4 times to remove all activation chemical. After the last MES Buffer centrifugation, 2 mL of the Buffer containing 5% MeOP and 0.1% Tween® 20 (the "second Buffer") is added to the tubes for the re-suspension step. Additional second Buffer is added to 35 mL before sonication. The bead suspension is centrifuged at 19,000 rpm for 30 min. The supernatant is discarded. The final sonication used 12 mL of the second Buffer in each tube to give a 25 mg/mL dilution. Particle size is 277 nm as determined on a UPA instrument.

The EPRM chemibead is prepared in a manner similar to the method described in U.S. Pat. No. 6,153,442 and U.S. Patent Application Publication No. 20050118727A, the relevant disclosures of which are incorporated herein by reference. The EPRM chemibead comprises an aminodextran inner layer and a dextran aldehyde outer layer having free aldehyde functionalities. See, for example, U.S. Pat. Nos. 5,929,049, 7,179,660 and 7,172,906, the relevant disclosures of which are incorporated herein by reference. The reaction is carried out at a temperature of about 0 to about 40° C. for a period of about 16 to about 64 hours at a pH of about 5.5 to about 7.0, or about 6, in a buffered aqueous medium employing a suitable buffer such as, for example, MES. The reaction is quenched by addition of a suitable quenching agent such as, for example, carboxymethoxyamine hemihydrochloride (CMO), and subsequent washing of the particles.

Aldehyde groups on the outer dextran aldehyde layer are reacted with ethylene diamine under reductive amination conditions to form reagent EPRM-EDA having pendant moieties comprising an ethylene chain and a terminal amine group. The reductive amination conditions include the use of a reducing agent such as, for example, a metal hydride. The reaction is carried out in an aqueous medium at a temperature during the reaction of about 20° C. to about 100° C. for a period of about 1 hour to about 48 hours.

Synthesis of 25(OH)D$_3$-3-Carbamate (25(OH)D$_3$-3-Carbamate)—a mixture of 22 mg (55 µmol) 25(OH)D$_3$ purchased from ChemReagents.com, Sugarland Tex., 100 mg (420 µmol) disuccinimidyl carbonate (DSC), 100 µL triethylamine in 1 mL anhydrous acetonitrile in a 5-mL flask (covered with foil) was stirred at room temperature for 18 hr under nitrogen to prepare activated 25(OH)D$_3$. TLC (EtOAc:Hexane=2:1) showed no starting material left. A suspension was prepared by adding 150 mg of carboxymethoxylamine hemihydrochloride (CMO), 0.3 ml triethylamine and 1 ml DMF to a 10 ml flask. A solution containing activated 25(OH)D$_3$ was added dropwise to the CMO suspension with stirring, which was continued for another 18 hr. Vacuum was applied to remove the solvents as much as possible (keeping the heating bath temperature below 50° C.). EtOAc (25 ml) was added to the residue, which was washed three times with 2 ml brine. The organic phase was dried with anhydrous Na$_2$SO$_4$ and was filtered; solvent was removed using a rotavap. Crude product (42 mg) was obtained after drying and was purified by HPLC. Pure product (24 mg) was obtained after drying under high vacuum. The product was dissolved into 1.2 ml anhydrous DMSO. Aliquots were transferred into vials, which were kept at −70° C.

Coupling EPRM-EDA with the hapten 25(OH)D$_3$-Carbamate—1.2 mg hapten was added to a 2-mL vial. 11.2 mg EDAC and 15.5 mg SNHS plus 3.73 mL dry DMSO was added to a 5-mL vial. EDAC/SNHS solution was rotated to dissolve contents. 1.14 mL EDAC/SNHS solution was added to the vial containing hapten. The mixture was rotated for 22 hours. EPRM-EDA (200 mg) was washed once with High pH Wash Buffer and then with MES pH6 buffer. To a 5-mL vial was added 1.08 mL (100 mg) of wash buffer followed by 143 mL 1.6% GAFAC® surfactant. To a small test tube was added 256 dry DMSO followed by 49 µL EDAC/SNHS/hapten. The DMSO/hapten solution was added drop-wise to the bead mixture (subjected to vortexing during addition). The bead/hapten mixture was rotated overnight at room temperature.

The bead/hapten mixture was transferred to a 50-mL centrifuge tube and diluted to 35 mL with 10% 1-methoxy-2-propanol/1% GAFAC® surfactant/MES pH6 buffer. The tube was centrifuged at 18,500 rpm at 10° C. for 30 min. The supernatant was discarded and replaced by 1 mL of the same buffer. The pellet was re-suspended with a stir-rod. The vial was filled to 35 mL with the same buffer. The tube was sonicated at 18-21 Watts for 1 minute using ice to keep the tube cold. The centrifugation/washing was repeated six times. Following the sixth wash, the buffer was switched to Hapten Wash Buffer pH7.2 and two more washings performed. Following the last wash and re-suspension with 1 mL Hapten wash buffer, 4 mL Hapten Wash Buffer was added. The bead mixture was sonicated at 50% power in a cup sonicator. Particle size was measured by UPA as 298 nm. Percent solids assay was performed and the bead mixture was diluted to 10 mg/mL. This Chemibead Reagent was formulated in 50 mM MES buffer.

Biotinylation of anti-25(OH)D antibody—NHS-PEO$_4$-biotin (Pierce Chemical Company, Rockford Ill.) was coupled with the anti-25(OH)D antibody (a sheep monoclonal antibody from Bioventix, Farnham, Surrey, UK). 3 mg of the anti-25(OH)D antibody was buffer-exchanged twice with 10 ml each of Antibody Dialysis Buffer (10 mM NaH$_2$PO$_4$ pH 7.0/300 mM NaCl) in 10 mL Amicon and then concentrated to 3.0 mg/mL. 1 mg of NHS-PEO4-biotin was dissolved in 100 µL Antibody Dialysis Buffer to make 10 mg/mL of the biotin reagent solution, which was added (35 µL) to the anti-25(OH)D antibody solution. The reaction mixture was rocked at room temperature overnight. The mixture was washed three times with 10 mL each of Antibody Dialysis Buffer in 10 mL Amicon, and then concentrated to about 1 mL. The concentration was measured on UV A280. The biotinylated anti-25(OH)D antibody reagent was formulated in an aqueous buffer containing 25 mM citric acid buffer, 300 mM NaCl, 1 mM EDTA, blocking proteins and preservatives, pH 5.0.

Sensibeads—Streptavidin-sensitizer bead was prepared using a method analogous to that described in U.S. Pat. Nos. 6,153,442, 7,022,529, 7,229,842 and U.S. Patent Application Publication No. 20050118727A. The photosensitizer was bis-(trihexyl)-silicon-t-butyl-phthalocyanine. The concentration of Sensibead reagent was 200 μg/mL in HEPES buffer, pH 8.0 containing 150 mM NaCl.

Releasing Reagent—sodium salicylate in 5 mM HEPES buffer.

Results of Immunoassay

The effect of adding anti-3-epimer-VD antibody 8F10.1 (anti-3-epimer VD Ab) on the 3-epimer cross-reactivity for the assay is shown in Table 1. Ten patient sera containing $25(OH)D_2$ or $25(OH)D_3$ compounds were spiked with 100 ng/mL of 3-epimer vitamin $D_3$ compound purchased from Sigma (Stock No. 751324). The 3-epimer cross-reactivity was calculated by the difference between $25(OH)D_2$ or $25(OH)D_3$ values with and without the spiked 3-epimer compound divided by the amount of added 3-epimer compound. With addition of 100 μg/mL of the anti-3-epimer-VD antibody 8F10.1, the average 3-epimer cross-reactivity was reduced from 13.7% to less than 2%.

Example 4

Immunoassay for 3-Epi-25OH Vitamin D

Immunoassay Procedure

The measurement of 3-epi-25OH Vitamin D (3-epi-25(OH)D) employed a homogeneous competitive chemiluminescent immunoassay based on LOCI® assay technology similar to that described above in Example 3. The assay was performed on the Siemens Dimension® EXL automated integrated clinical chemistry system (Siemens Healthcare Diagnostics Inc. The LOCI® assay reagents utilized for the measurement of 3-epi-25(OH)D included a releasing reagent, two synthetic bead reagents and a biotinylated monoclonal anti-3-epimer antibody reagent. The first bead reagent (Sensibeads) was coated with streptavidin and contained photosensitive dye. The second bead reagent (Chemibeads) was coated with a 3-epimer analog (compound of the Formula IIa above wherein Z' is a non-poly(amino acid) label, namely, EPRM-EDA chemibead) prepared in a manner similar to the described above for Example 1. Sample was incubated with the releasing reagent to release 25(OH)D molecules including 3-epimeric compounds from vitamin D binding proteins. The reaction mixture was then incubated with biotinylated antibody to form a 3-epi-25(OH)D/biotinylated antibody complex. Chemibeads were added to scavenge the excess free biotinylated antibody. Sensibeads are then added and bind to the biotin portion of the biotinylated antibody. Aggregates of Chemibead-analog/antibody-biotin/streptavidin-Sensibeads were formed as a result. Illumination of the reaction mixture by light at 680 nm generated singlet oxygen from the Sensibeads, which diffused into the Chemibeads and triggered a chemiluminescent reaction. The resulting chemiluminescent signal is measured at 612 nm and is inversely proportional to the concentration of total 3-epi-25(OH)D in the sample.

Preparation of Reagents for Immunoassay

Synthesis of 3-epimer analog Chemibeads—Chemibeads for use in this assay for the detection of 3-epi-25(OH)D were prepared in a manner similar to that described above in

TABLE 1

| | | No anti-3-epimer VD Ab Added | | Anti-3-epimer VD Ab Added | |
|---|---|---|---|---|---|
| Sample ID | 3-epimer D3 Spiked | ng/mL | Cross-Reactivity | ng/mL | Cross-Reactivity |
| 1 | No | 30.2 | | 30.7 | |
|   | Yes | 48.0 | 17.9% | 33.0 | 2.2% |
| 2 | No | 22.5 | | 23.2 | |
|   | Yes | 40.5 | 17.9% | 25.6 | 2.4% |
| 3 | No | 19.8 | | 20.7 | |
|   | Yes | 31.6 | 11.9% | 22.5 | 1.8% |
| 4 | No | 40.4 | | 40.5 | |
|   | Yes | 53.0 | 12.6% | 41.4 | 1.0% |
| 5 | No | 46.6 | | 45.6 | |
|   | Yes | 62.7 | 16.1% | 49.2 | 3.5% |
| 6 | No | 47.3 | | 48.5 | |
|   | Yes | 57.5 | 10.2% | 46.4 | −2.0% |
| 7 | No | 53.1 | | 55.4 | |
|   | Yes | 62.2 | 9.1% | 55.4 | 0.0% |
| 8 | No | 39.5 | | 40.8 | |
|   | Yes | 50.0 | 10.5% | 43.8 | 3.0% |
| 9 | No | 47.4 | | 48.6 | |
|   | Yes | 62.8 | 15.3% | 50.8 | 2.2% |
| 10 | No | 23.6 | | 24.8 | |
|   | Yes | 39.1 | 15.5% | 28.6 | 3.8% |
| | Avg. Cross-reactivity | | 13.7% | | 1.8% |

Figure 9:
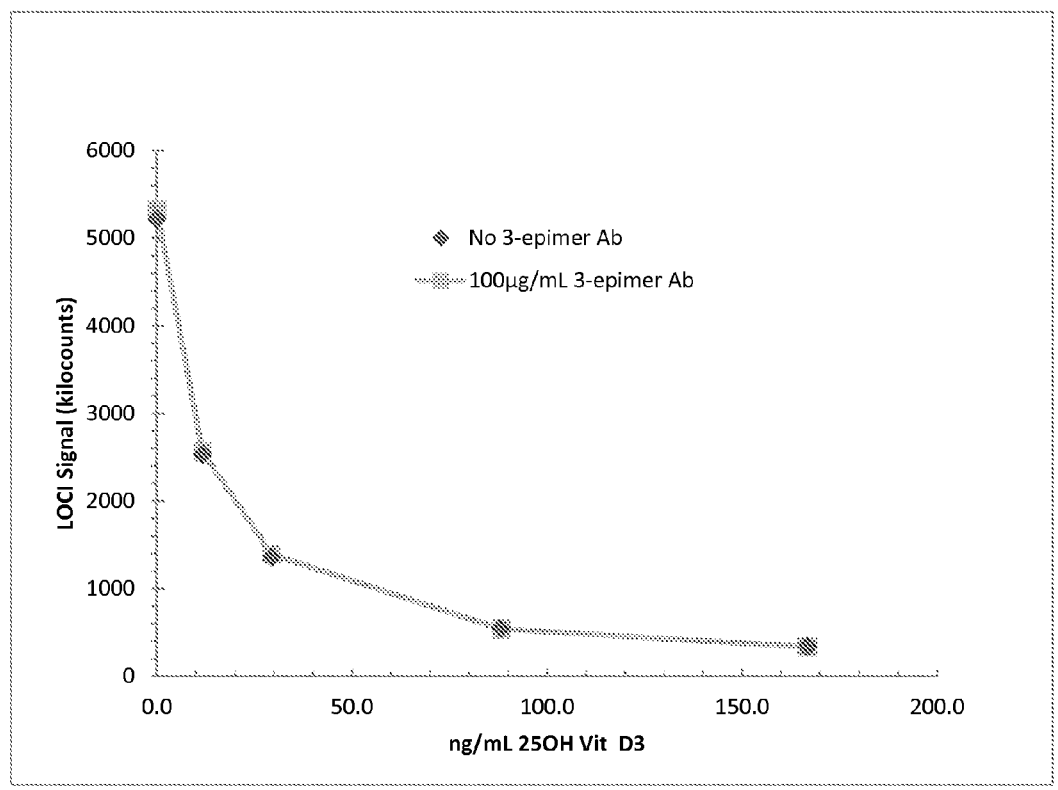
FIG. 9 illustrates a comparison of standard curves generated using reagents with and without added anti-3-epimer-VD antibody.

FIG. 9 illustrates a comparison of standard curves generated using reagents with and without added anti-3-epimer-VD antibody 8F10.1 (3-epimer Ab). The complete overlap of the two curves shows that the anti-3-epimer-VD antibody 8F10.1 does not affect the measurement of $25(OH)D_3$ (25OH Vit D3 in FIG. 9), indicating the antibody is specific to the 3-epimer compound and has no observable cross-reactivity with the $25(OH)D_3$.

Example 3 for Synthesis of 25(OH)D3 Chemibeads with the hapten being a compound of the Formula IIa where Z' is the chemibead.

Chemibead Reagent—3-epimer analog Chemibeads in 50 nM MES buffer.

Biotinylation of anti-3-epimer-VD antibody 8F10.1—Biotinylation of the anti-3-epimer-VD antibody 8F10.1 was carried out in a manner similar to that described above in Example 3 for the Biotinylation of anti-25(OH)D antibody.

Biotinylated Antibody Reagent—Biotinylated anti-3-epimer-VD antibody 8F10.1 stated above in 25 mM citric buffer.

Sensibead Reagent—Sensibead Reagent was the same as in Example 3.

Results of Immunoassay

Figure 10:
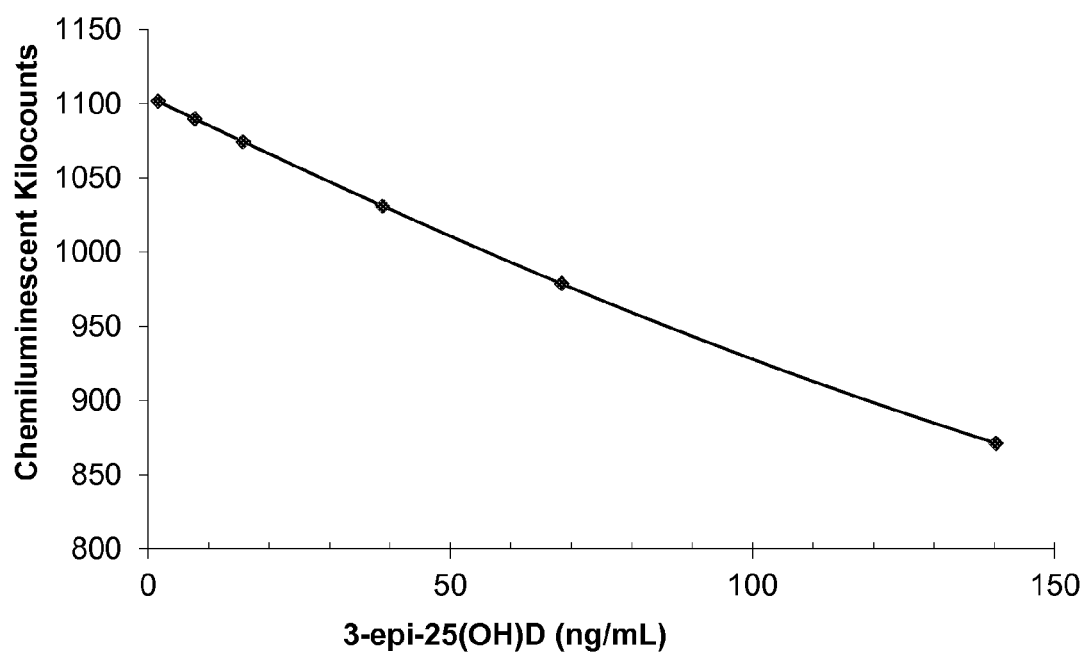
FIG. 10 is a standard curve for an immunoassay for determination of 3-epi-25(OH)D in samples using anti-3-epimer-VD antibody.

FIG. 10 illustrates a standard curve for the immunoassay for the determination of 3-epi-25(OH)D in samples using anti-3-epimer-VD antibody 8F10.1. Chemiluminescent Kilocounts represents the chemiluminescent signal measured as described above.

All publications and patent applications cited in this specification are herein incorporated by reference as if each individual publication or patent application were specifically and individually indicated to be incorporated by reference.

It should be understood that the above-described examples are merely illustrative of some of the many specific examples that represent the principles described herein. Clearly, those skilled in the art can readily devise numerous other arrangements without departing from the scope as defined by the following claims.

What is claimed is:

1. A binding partner prepared against a compound of the formula:

$(R^1)_p\text{-}(L)_q\text{-}Z$ wherein $R^1 =$ 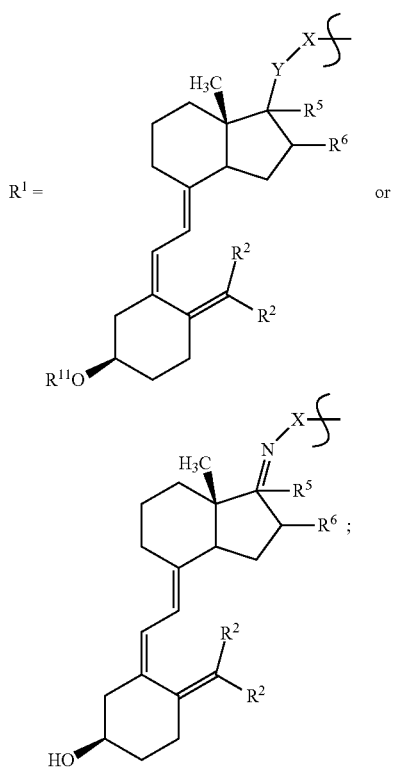 or

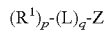 represents linkage to L,

Y is O, S, CR, or NR$^4$,

X is —O—(CH$_2$)$_n$—C(O)—, —(CH$_2$)$_w$—C(O)—, —(CH$_2$)$_w$—C(O)—(CH$_2$)$_x$—C(O)—, —(CH$_2$)$_w$—C(O)—NH(CH$_2$)$_y$—C(O)—, or —NR$^3$—C(O)—,

R is independently H or alkyl,

R$^2$ is H,

R$^3$ and R$^4$ are independently H or alkyl,

R$^5$ and R$^6$ are H,

R$^{11}$ is H, n is an integer from 0 to 10, w is an integer from 1 to 10, x is an integer from 1 to 10, y is an integer from 1 to 10, p is 1, L is a linking group, q is 0 or 1, Z is an immunogenic carrier; and wherein said binding partner is an antibody that specifically binds to 3-epi-25-hydroxyvitamin D but does not bind to any detectable degree with 25-hydroxyvitamin D.

2. The binding partner according to claim 1 wherein in the compound $R^1 =$ 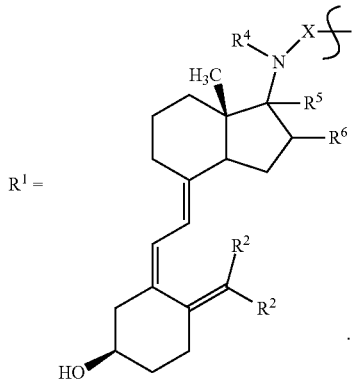

3. The binding partner according to claim 1 wherein in the compound $R^1 =$ 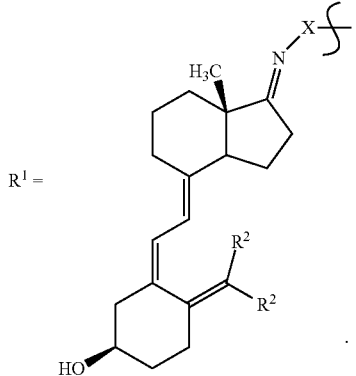

4. An antibody that is specific for 3-epi-25-hydroxyvitamin D$_3$ and does not bind to any detectable degree to non-epi-vitamin D compounds, wherein the non-epi-vitamin D compounds are 25-hydroxyvitamin D; calcidiol; 1,25-dihydroxyvitamin $D_3$; 1,25-dihydroxy vitamin $D_4$; 1,25-dihydroxy vitamin $D_5$; and 1,25-dihydroxy vitamin $D_6$.

5. A method of separating an epimeric vitamin D from a sample suspected of containing an epimeric vitamin D, the method comprising:
  contacting a aqueous medium comprising the sample with an affinity chromatography medium to which is bound an antibody according to claim 4 to capture the epimeric vitamin D, and
  separating the aqueous medium from the affinity chromatography medium.

6. The method according to claim 5 further comprising separating the epimeric vitamin D from the affinity chromatography medium.

* * * * *